US012606537B2

(12) United States Patent
Leiendecker et al.

(10) Patent No.: US 12,606,537 B2
(45) Date of Patent: Apr. 21, 2026

(54) THIOPHENE DERIVATIVES

(71) Applicants: Merck Patent GmbH, Darmstadt (DE); Ryvu Therapeutics S.A., Cracow (PL)

(72) Inventors: Matthias Leiendecker, Darmstadt (DE); Hans-Peter Buchstaller, Darmstadt (DE); Thomas Fuchss, Darmstadt (DE)

(73) Assignees: Ryvu Therapeutics S.A., Cracow (PL); MerckPatent GmbH, Darmstadt (DE)

( * ) Notice: Subject to any disclaimer, the term of this patent is extended or adjusted under 35 U.S.C. 154(b) by 939 days.

(21) Appl. No.: 17/756,391

(22) PCT Filed: Nov. 24, 2020

(86) PCT No.: PCT/EP2020/083110

§ 371 (c)(1),
(2) Date: May 24, 2022

(87) PCT Pub. No.: WO2021/105069

PCT Pub. Date: Jun. 3, 2021

(65) Prior Publication Data

US 2023/0024721 A1 Jan. 26, 2023

(30) Foreign Application Priority Data

Nov. 26, 2019 (EP) .................................... 19211370

(51) Int. Cl.
*C07D 333/60* (2006.01)

(52) U.S. Cl.
CPC .................................. *C07D 333/60* (2013.01)

(58) Field of Classification Search
None
See application file for complete search history.

(56) References Cited

U.S. PATENT DOCUMENTS 11,613,526 B2 * 3/2023 Leiendecker ...... A61K 31/4436 514/337

FOREIGN PATENT DOCUMENTS

| | | | |
|---|---|---|---|
| WO | 2015/035223 | 3/2015 | |
| WO | 2016/144825 | 9/2016 | |
| WO | 2016/144826 | 9/2016 | |
| WO | 2016/145032 | 9/2016 | |
| WO | 2016/145045 | 9/2016 | |
| WO | 2016/168510 | 10/2016 | |
| WO | 2018/031680 | 2/2018 | |
| WO | 2019/191227 | 10/2019 | |
| WO | WO-2019191227 A1 * | 10/2019 | ........... A61K 31/085 |
| WO | 2019/219731 | 11/2019 | |

OTHER PUBLICATIONS

Patani et al., Chemical Reviews 1996 96 (8), 3147-3176 (Year: 1996).*
Allan B. Foster, "Deuterium Isotope Effects in the Metabolism of Drugs and Xenobiotics: Implications for Drug Design", Advances in Drug Research, vol. 14, 1985, pp. 1-40.
Chen et al., "Targeting renal cell carcinoma with a HIF-2 antagonist", Nature, vol. 539, Nov. 3, 2016, pp. 112-117.
Cho et al., "On-target efficacy of a HIF-2α antagonist in preclinical kidney cancer models", Nature, vol. 539, Nov. 3, 2016, pp. 107-111.
Gillette et al., "Theory for the Observed Isotope Effects on the Formation of Multiple Products by Different Kinetic Mechanisms of Cytochrome P450 Enzymes", Biochemistry, vol. 33, No. 10, 1994, pp. 2927-2937.
Hanzlik et al., "Active Site Dynamics of Toluene Hydroxylation by Cytochrome P-450[1]", Journal Org. Chem., vol. 55, No. 13, 1990, pp. 3992-3997.
International Search Report dated Jan. 28, 2021 in PCT/EP2020/083110, 4 pages.
Jarman et al., "The deuterium isotope effect for the α-hydroxylation of tamoxifen by rat liver microsomes accounts for the reduced genotoxicity of [$D_5$-ethyl]tamoxifen", Carcinogenesis, vol. 16, No. 4, 1995, pp. 683-688.
Reider et al., "Synthesis of (R)-Serine-2-d and Its Conversion to the Broad Spectrum Antibiotic Fludalanine", Journal Org. Chem., vol. 52, No. 15, 1987, pp. 3326-3334.
Wilkins et al., "Targeting Protein-Protein Interactions in the HIF System", ChemMedChem, vol. 11, 2016, pp. 773-786.
Written Opinion dated Jan. 28, 2021 in PCT/EP2020/083110, 6 pages.

* cited by examiner

*Primary Examiner* — Jeffrey S Lundgren
*Assistant Examiner* — Anthony Joseph Seitz
(74) *Attorney, Agent, or Firm* — EMD Serono Research Institute

(57) ABSTRACT

Compounds of the formula I

I

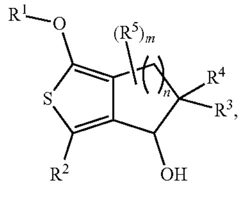

are inhibitors of HIF-2α, and can be employed for the treatment of diseases such as cancer.

16 Claims, No Drawings

THIOPHENE DERIVATIVES

CROSS-REFERENCE TO RELATED APPLICATIONS

This application is the National Stage entry under § 371 of International Application No. PCT/EP2020/083110, filed on Nov. 24, 2020, and which claims the benefit of priority to European Application No. 19211370.2, filed on Nov. 26, 2019. The content of each of these applications is hereby incorporated by reference in its entirety.

BACKGROUND OF THE INVENTION

The invention had the object of finding novel compounds having valuable properties, in particular those which can be used for the preparation of medicaments.

The present invention relates to thiophene derivatives which inhibit HIF-2α (HIF-2alpha) (Hypoxia-Inducible Factor). The compounds of this invention are therefore useful in treating diseases such as cancer.

The present invention also provides methods for preparing these compounds, pharmaceutical compositions comprising these compounds, and methods of treating diseases utilizing pharmaceutical compositions comprising these compounds.

An adequate supply of oxygen to tissues is essential in maintaining mammalian cell function and physiology. A deficiency in oxygen supply to tissues is a characteristic of a number of pathophysiologic conditions in which there is insufficient blood flow to provide adequate oxygenation, for example, ischemic disorders, cancer, and atherosclerosis. The hypoxic (low oxygen) environment of tissues activates a signaling cascade that drives the induction or repression of the transcription of a multitude of genes implicated in events such as angiogenesis (neo-vascularization), glucose metabolism, and cell survival/death. A key to this hypoxic transcriptional response lies in the transcription factors, the hypoxia-inducible factors (HIF).

HIFs are disregulated in a vast array of cancers through hypoxia-dependent and independent mechanisms and expression is associated with poor patient prognosis. Hypoxia inducible factors (HIFs), including HIF-1α and HIF-2α, are transcription factors that mediate cellular responses to diminished oxygen supply. These proteins become stabilized under hypoxia (low oxygen) and subsequently activate the expression of genes to facilitate cell survival and proliferation. HIF proteins are activated in many types of cancers and have been implicated in cancer initiation, progression, and metastasis. The role of HIF-2α is particularly important in clear cell renal cell carcinoma (ccRCC). In the majority of ccRCC tumors, the tumor suppressor von Hippel-Lindau protein (pVHL) that targets HIF-2α for degradation is inactivated, leading to the accumulation of HIF-2α and the transcription of genes that drive kidney cancer tumorigenesis. Certain cancers including renal cell carcinoma show high levels of HIF-2α and a dependency on HIF-2α signaling.

HIF-2α protein has been detected in various human tumors of the bladder, breast, colon, liver, ovaries, pancreas, prostate, and kidney as well as tumor-associated macrophages.

Compounds of this invention show high activity against HIF-2α in multiple relevant settings including biochemical, biophysical and cellular assays.

It has been found that the compounds according to the invention and salts thereof have very valuable pharmacological properties while being well tolerated.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

The susceptibility of a particular cell to treatment with the compounds according to the invention can be determined by in vitro tests. Typically, a culture of the cell is combined with a compound according to the invention at various concentrations for a period of time which is sufficient to allow active agents such as anti IgM to induce a cellular response such as expression of a surface marker, usually between about one hour and one week. In vitro testing can be carried out using cultivated cells from blood or from a biopsy sample. The amount of surface marker expressed is assessed by flow cytometry using specific antibodies recognising the marker.

The dose varies depending on the specific compound used, the specific disease, the patient status, etc. A therapeutic dose is typically sufficient considerably to reduce the undesired cell population in the target tissue while the viability of the patient is maintained. The treatment is generally continued until a considerable reduction has occurred, for example an at least about 50% reduction in the cell burden, and may be continued until essentially no more undesired cells are detected in the body.

PRIOR ART

Other HIF-2α inhibitors for the treatment of cancer are described in WO 2018/031680 A1, WO 2015/035223 A1, WO 2016/145045 A1, WO 2016/145032 A1, WO 2016/144825 A1, WO 2016/144826 A1 and WO 2016/168510 A1.

Preclinical on-target efficacies studies of a HIF-2α antagonist are described by H. Cho et al. Nature, Vol. 539, 2016, 107-122 (doi:10.1038/nature19795) and by W. Chen et al. Nature, Vol. 539, 2016, 112-130 (doi:10.1038/naturel 9796).

A review on HIF-2α targeting approaches is described by S. E. Wilkins ChemMedChem, 2016, 11, 773-786.

SUMMARY OF THE INVENTION

The invention relates to compounds of the formula I

I

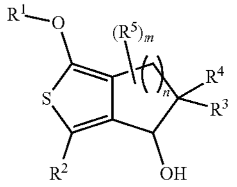

In which $R^1$ denotes A, $[C(R^6)_2]_q$Ar, $[C(R^6)_2]_q$Cyc, $[C(R^6)_2]_q$Het or COA, $R^2$ denotes $SO_2A$, SOA, SA, $SO_2NHA$, $SO_2NA_2$, S(=NH, =O)A, $S(=NH)_2A$, $NO_2$, Hal, CN, A, $Het^1$, COOH or COOA, $R^3$ denotes H or Hal, $R^4$ denotes H or Hal, $R^5$ denotes H or Hal, $R^6$ denotes H or A', A denotes unbranched or branched alkyl having 1-8 C-atoms, in which 1-5 H atoms may be replaced by OH, OA, F, Cl and/or Br and/or in which one or two non-adjacent $CH_2$ groups may be replaced by O and/or NH groups, A' denotes unbranched or branched alkyl having 1, 2, 3 or 4 C-atoms, Cyc denotes cyclic alkyl with 3, 4, 5, 6 or 7 C-atoms, in which 1-5 H atoms may be replaced by OH, OA, F and/or Cl, Ar denotes phenyl, which is unsubstituted or mono-, di- or trisubstituted by Hal, A, $NH_2$, NHA, $NA_2$, COOH, COOA, $CONH_2$, CONHA, $CONA_2$, CONHAr, $S(O)_pA$, $NHCH_2Ar$, CN, OH and/or OA, Het denotes a mono- or bicyclic aromatic, unsaturated or saturated heterocycle having 1 to 4 N, O and/or S atoms, which may be unsubstituted or mono-, di- or trisubstituted by Hal, A, $NH_2$, NHA, $NA_2$, COOH, COOA, $CONH_2$, CONHA, $CONA_2$, CONHAr, $S(O)_pA$, $NHCH_2Ar$, CN, OH and/or OA, $Het^1$ denotes a mono- or bicyclic aromatic, unsaturated or saturated heterocycle having 1 to 4 N, O and/or S atoms, which may be unsubstituted or mono-, di- or trisubstituted by Hal, A, COOA, $NH_2$, NHA and/or $NA_2$, Hal denotes F, Cl, Br or I, n denotes 1 or 2, m denotes 0, 1, 2 or 3, p denotes 1, 2 or 3, q denotes 0, 1 or 2, and pharmaceutically acceptable solvates. salts, tautomers and stereoisomers thereof, including mixtures thereof in all ratios.

The invention also relates to the optically active forms (stereoisomers), the enantiomers, the racemates, the diastereomers and the hydrates and solvates of these compounds.

Moreover, the invention relates to pharmaceutically acceptable derivatives of compounds of formula I.

DETAILED DESCRIPTION OF THE INVENTION

The term solvates of the compounds is used to describe adductions of inert solvent molecules onto the compounds which form owing to their mutual attractive force. Solvates are, for example, mono- or dihydrates or alkoxides.

It is understood, that the invention also relates to the solvates of the salts.

The term pharmaceutically acceptable derivatives is taken to mean, for example, the salts of the compounds according to the invention and also so-called prodrug compounds.

As used herein and unless otherwise indicated, the term "prodrug" means a derivative of a compound of formula I that can hydrolyze, oxidize, or otherwise react under biological conditions (in vitro or in vivo) to provide an active compound, particularly a compound of formula I. Examples of prodrugs include, but are not limited to, derivatives and metabolites of a compound of formula I that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. In certain embodiments, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger's Medicinal Chemistry and Drug Discovery 6th ed. (Donald J. Abraham ed., 2001, Wiley) and Design and Application of Prodrugs (H. Bundgaard ed., 1985, Harwood Academic Publishers Gmfh).

The expression "effective amount" denotes the amount of a medicament or of a pharmaceutical active ingredient which causes in a tissue, system, animal or human a biological or medical response which is sought or desired, for example, by a researcher or physician.

In addition, the expression "therapeutically effective amount" denotes an amount which, compared with a corresponding subject who has not received this amount, has the following consequence:

improved treatment, healing, prevention or elimination of a disease, syndrome, condition, complaint, disorder or side-effects or also the reduction in the advance of a disease, complaint or disorder.

The expression "therapeutically effective amount" also encompasses the amounts which are effective for increasing normal physiological function.

The invention also relates to the use of mixtures of the compounds of the formula I, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution.

The invention relates to the compounds of the formula I and salts thereof and to a process for the preparation of compounds of the formula I and pharmaceutically acceptable salts, solvates, tautomers and stereoisomers thereof, characterised in that a)

a compound of the formula II

II

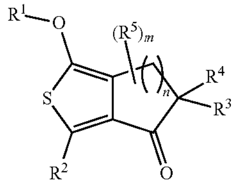

in which $R^1$, $R^2$, $R^3$, $R^4$, $R^5$, m and n have the meanings indicated for formula I above, is reacted with $NaBH_4$ or any other reducing agent and/or a base or acid of the formula I is converted into one of its salts.

Above and below, the radicals $R^1$, $R^2$, $R^3$, $R^4$, $R^5$, m and n have the meanings indicated for the formula I, unless explicitly stated otherwise.

A denotes alkyl, this is unbranched (linear) or branched, and has 1, 2, 3, 4, 5, 6, 7 or 8 C atoms. A preferably denotes methyl, ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, furthermore preferably, for example, trifluoromethyl.

A very particularly preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl.

Moreover, A denotes preferably $CH_2OCH_3$, $CH_2CH_2OH$ or $CH_2CH_2OCH_3$.

Moreover, A denotes preferably unbranched or branched alkyl having 1-6 C-atoms, in which 1-5 H atoms may be replaced by OH and/or F, and/or in which one or two non-adjacent $CH_2$ groups may be replaced by O and/or NH groups.

A' preferably denotes alkyl having 1, 2, 3 or 4 C atoms, preferably methyl, ethyl, propyl, isopropyl, butyl, isobutyl, sec-butyl or tert-butyl.

$R^1$ preferably denotes A, $[C(R^6)_2]_q$Ar, $[C(R^6)_2]_q$Cyc or $[C(R^6)_2]_q$Het.

$R^2$ preferably denotes $SO_2A$, most preferably $SO_2CH_3$.

$R^3$ preferably denotes H or F.

$R^4$ preferably denotes H or F.

$R^5$ preferably denotes H.

Cyc preferably denotes cyclopropyl, cyclobutyl, cyclopentyl, cyclohexyl or cycloheptyl, in which 1-5 H atoms may be replaced by OH, OA, F and/or Cl.

Irrespective of further substitutions, Het denotes, for example, 2- or 3-furyl, 2- or 3-thienyl, 1-, 2- or 3-pyrrolyl, 1-, 2, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, indazolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7- benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxa-diazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, pyrrolopyridinyl, purinyl, further preferably 1,3-benzodioxol-5-yl, 1,4-benzodioxan-6-yl, 2,1,3-benzothiadiazol-4- or -5-yl, 2,1,3-benzoxadiazol-5-yl, azabicyclo[3.2.1]-octyl or dibenzofuranyl.

The heterocyclic radicals may also be partially or fully hydrogenated.

Irrespective of further substitutions, Het can thus also denote, for example, 2,3-dihydro-2-, -3-, -4- or -5-furyl, 2,5-dihydro-2-, -3-, -4- or 5-furyl, tetra-hydro-2- or -3-furyl, 1,3-dioxolan-4-yl, tetrahydro-2- or -3-thienyl, 2,3-di-hydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetra-hydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, furthermore preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or 6-yl, 2,3-(2-oxomethylenedioxy)phenyl or also 3,4-dihydro-2H-1,5-benzodioxepin-6- or -7-yl, furthermore preferably 2,3-dihydrobenzofuranyl, 2,3-dihydro-2-oxofuranyl, 3,4-dihydro-2-oxo-1H-quinazolinyl, 2,3-dihydrobenzoxazolyl, 2-oxo-2,3-dihydrobenzoxazolyl, 2,3-dihydrobenzimidazolyl, 1,3-dihydroindole, 2-oxo-1,3-dihydroindole or 2-oxo-2,3-dihydrobenzimidazolyl.

Irrespective of further substitutions, $Het^1$ denotes, for example, 2- or 3-furyl, 2- or 3-thienyl, 1-, 2- or 3-pyrrolyl, 1-, 2, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, indazolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7- benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxa-diazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, pyrrolopyridinyl, purinyl, further preferably 1,3-benzodioxol-5-yl, 1,4-benzodioxan-6-yl, 2,1,3-benzothiadiazol-4- or -5-yl, 2,1,3-benzoxadiazol-5-yl, azabicyclo[3.2.1]-octyl or dibenzofuranyl.

The heterocyclic radicals may also be partially or fully hydrogenated.

Irrespective of further substitutions, Het' can thus also denote, for example, 2,3-dihydro-2-, -3-, -4- or -5-furyl, 2,5-dihydro-2-, -3-, -4- or 5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, furthermore preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or 6-yl, 2,3-(2-oxomethylenedioxy)phenyl or also 3,4-dihydro-2H-1,5-benzodioxepin-6- or -7-yl, furthermore preferably 2,3-dihydrobenzofuranyl, 2,3-dihydro-2-oxofuranyl, 3,4-dihydro-2-oxo-1 H-quinazolinyl, 2,3-dihydrobenzoxazolyl, 2-oxo-2,3-dihydrobenzoxazolyl, 2,3-dihydrobenzimidazolyl, 1,3-dihydroindole, 2-oxo-1,3-dihydroindole or 2-oxo-2,3-dihydrobenzimidazolyl.

Het preferably denotes a monocyclic saturated heterocycle having 1 to 4 N, O and/or S atoms, which may be unsubstituted or mono-, di- or trisubstituted by Hal, A, CN, OH and/or OA.

Het particularly preferably denotes tetrahydrofuryl, 1,3-dioxolanyl, tetrahydro-thienyl, pyrrolidinyl, piperidinyl, morpholinyl, tetrahydro-pyranyl or piperazinyl.

Ar denotes, for example, phenyl, o-, m- or p-tolyl, o-, m- or p-ethylphenyl, o-, m- or p-propylphenyl, o-, m- or p-isopropylphenyl, o-, m- or p-tert-butyl-phenyl, o-, m- or p-hydroxyphenyl, o-, m- or p-nitrophenyl, o-, m- or p-aminophenyl, o-, m- or p-(N-methylamino)phenyl, o-, m- or p-(N-methyl-aminocarbonyl)phenyl, o-, m- or p-acetamidophenyl, o-, m- or p-methoxyphenyl, o-, m- or p-ethoxyphenyl, o-, m- or p-ethoxycarbonylphenyl, o-, m- or p-(N,N-dimethylamino)phenyl, o-, m- or p-(N,N-dimethylaminocarbonyl)phenyl, o-, m- or p-(N-ethylamino)phenyl, o-, m- or p-(N,N-diethylamino)phenyl, o-, m- or p-fluorophenyl, o-, m- or p-bromophenyl, o-, m- or p-chlorophenyl, o-, m- or p-(methylsulfonamido)phenyl, o-, m- or p-(methylsulfonyl)phenyl, o-, m- or p-cyanophenyl, o-, m- or p-carboxy-phenyl, o-, m- or p-methoxycarbonylphenyl, o-, m- or p-aminosulfonylphenyl, o-, m- or p-(benzylamino)phenyl furthermore preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromo-phenyl, 2,4- or 2,5-dinitrophenyl, 2,5- or 3,4-dimethoxyphenyl, 3-nitro-4-chlorophenyl, 3-amino-4-chloro-, 2-amino-3-chloro-, 2-amino-4-chloro-, 2-amino-5-chloro- or 2-amino-6-chlorophenyl, 2-nitro-4-N,N-dimethylamino- or 3-nitro-4-N,N-dimethylaminophenyl, 2,3-diaminophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-chloro-4-acetamidophenyl, 3-fluoro-4-methoxyphenyl, 3-amino-6-methylphenyl, 3-chloro-4-acetamidophenyl or 2,5-dimethyl-4-chlorophenyl.

Ar particularly preferably denotes phenyl which is unsubstituted or mono-, di- or trisubstituted by Hal and/or CN.

Particularly preferred compounds of formula I are

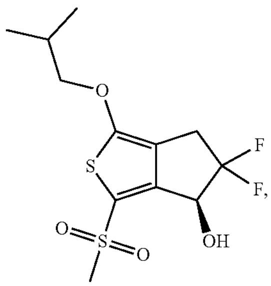

,

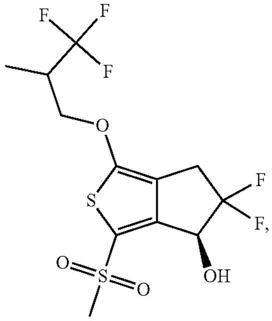

,

-continued

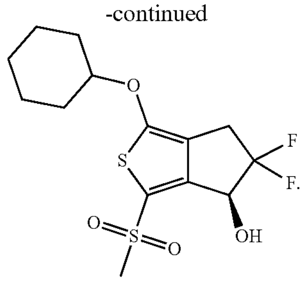

.

Throughout the invention, all radicals which occur more than once may be identical or different, i.e. are independent of one another.

The compounds of the formula I may have one or more chiral centres and can therefore occur in various stereoisomeric forms. The formula I encompasses all these forms.

Accordingly, the invention relates, in particular, to the compounds of the formula I in which at least one of the said radicals has one of the preferred meanings indicated above. Some preferred groups of compounds may be expressed by the following sub-formulae Ia to Ih, which conform to the formula I and in which the radicals not designated in greater detail have the meaning indicated for the formula I, but in which

- in Ia $R^1$ denotes A, $[C(R^6)_2]_q$Ar, $[C(R^6)_2]_q$Cyc or $[C(R^6)_2]_q$Het;
- in Ib $R^2$ denotes $SO_2A$;
- in Ic $R^3$ denotes H or F,
  $R^4$ denotes H or F;
- in Id A denotes A denotes preferably unbranched or branched alkyl having 1-6 C-atoms, in which 1-5 H atoms may be replaced by OH and/or F, and/or in which one or two non-adjacent $CH_2$ groups may be replaced by O and/or NH groups;
- in Ie Ar denotes phenyl, which is unsubstituted or mono-, di- or trisubstituted by Hal and/or CN;
- in If Het denotes a monocyclic saturated heterocycle having 1 to 4 N, O and/or S atoms, which may be unsubstituted or mono-, di- or trisubstituted by Hal, A, CN, OH and/or OA;
- in Ig Het denotes tetrahydrofuryl, 1,3-dioxolanyl, tetrahydro-thienyl, pyrrolidinyl, piperidinyl, morpholinyl, tetrahydro-pyranyl or piperazinyl;
- in Ih $R^1$ denotes A, $[C(R^6)_2]_q$Ar, $[C(R^6)_2]_q$Cyc or $[C(R^6)_2]_q$Het;
  $R^2$ denotes $SO_2A$,
  $R^3$ denotes H or F,
  $R^4$ denotes H or F,
  $R^5$ denotes H,
  $R^6$ denotes H or A',
  A denotes unbranched or branched alkyl having 1-8 C-atoms, in which 1-5 H atoms may be replaced by OH and/or F, and/or in which one or two non-adjacent $CH_2$ groups may be replaced by 0 and/or NH groups,
  A' denotes unbranched or branched alkyl having 1, 2, 3 or 4 C-atoms,
  Cyc denotes cyclic alkyl with 3, 4, 5, 6 or 7 C-atoms, in which 1-5 H atoms may be replaced by OH, OA, F and/or Cl,
  Ar denotes phenyl, which is unsubstituted or mono-, di- or trisubstituted by Hal and/or CN,
  Het denotes tetrahydrofuryl, 1,3-dioxolanyl, tetrahydro-thienyl, pyrrolidinyl, piperidinyl, morpholinyl, tetrahydro-pyranyl or piperazinyl, Hal denotes F, Cl, Br or I,
n denotes 1 or 2,
m denotes 0, 1, 2 or 3,
p denotes 1, 2 or 3,
q denotes 0, 1 or 2, and pharmaceutically acceptable solvates, salts, tautomers and stereoisomers thereof, including mixtures thereof in all ratios.

The compounds of the formula I and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants known per se which are not mentioned here in greater detail.

Compounds of the formula I can preferably be obtained by reacting a compound of the formula II with a complex hydride such as $NaBH_4$ in an inert solvent such as MeOH or THF. The reaction is generally performed at temperatures between 0° C. and 75° C., preferably at 10° C. to 40° C.

Pharmaceutical Salts and Other Forms

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds of the formula I are for the most part prepared by conventional methods. If the compound of the formula I contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminium salts of the compounds of the formula I are likewise included. In the case of certain compounds of the formula I, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of the formula I include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, formate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese (III), manganese(II), potassium, sodium and zinc salts, but this is not intended to represent a restriction. Of the above-mentioned salts, preference is given to ammonium; the alkali metal salts sodium and potassium, and the alkaline earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, TEA, trimethylamine, tripropylamine and tris(hydroxymethyl)methylamine (tromethamine), but this is not intended to represent a restriction.

Compounds of the present invention which contain basic nitrogen-containing groups can be quaternised using agents such as ($C_1$-$C_4$)alkyl halides, for example methyl, ethyl, isopropyl and tert-butyl chloride, bromide and iodide; di($C_1$-$C_4$)alkyl sulfates, for example dimethyl, diethyl and diamyl sulfate; ($C_{10}$-$C_{18}$)alkyl halides, for example decyl, dodecyl, lauryl, myristyl and stearyl chloride, bromide and iodide; and aryl($C_1$-$C_4$)alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

Particular preference is given to hydrochloride, dihydrochloride, hydrobromide, maleate, mesylate, phosphate, sulfate and succinate.

The acid-addition salts of basic compounds of the formula I are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds of the formula I are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active ingredient which comprises a compound of the formula I in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

Isotopes

There is furthermore intended that a compound of the formula I includes isotope-labelled forms thereof. An isotope-labelled form of a compound of the formula I is identical to this compound apart from the fact that one or more atoms of the compound have been replaced by an atom or atoms having an atomic mass or mass number which differs from the atomic mass or mass number of the atom which usually occurs naturally. Examples of isotopes which are readily commercially available and which can be incorporated into a compound of the formula I by well-known methods include isotopes of hydrogen, carbon, nitrogen, oxygen, phosphorus, fluorine and chlorine, for example $^{2}H$, $^{3}H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. A compound of the formula I or a pharmaceutically acceptable salt of either which contains one or more of the above-mentioned isotopes and/or other isotopes of other atoms is intended to be part of the present invention. An isotope-labelled compound of the formula I can be used in a number of beneficial ways. For example, an isotope-labelled compound of the formula I into which, for example, a radioisotope, such as $^{3}H$ or $^{14}C$, has been incorporated is suitable for medicament and/or substrate tissue distribution assays. These radioisotopes, i.e. tritium ($^{3}H$) and carbon-14 ($^{14}C$), are particularly preferred owing to simple preparation and excellent detectability. Incorporation of heavier isotopes, for example deuterium ($^{2}H$), into a compound of the formula I has therapeutic advantages owing to the higher metabolic stability of this isotope-labelled compound. Higher metabolic stability translates directly into an increased in vivo half-life or lower dosages, which under most circumstances would represent a preferred embodiment of the present invention. An isotope-labelled compound of the formula I can usually be prepared by carrying out the procedures dis-closed in the synthesis schemes and the related description, in the example part and in the preparation part in the present text, replacing a non-isotope-labelled reactant by a readily available isotope-labelled reactant.

Deuterium ($^{2}H$) can also be incorporated into a compound of the formula I for the purpose in order to manipulate the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus cause a reduction in the rate in rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D$=2-7 are typical. If this rate difference is successfully applied to a compound of the formula I that is susceptible to oxidation, the profile of this compound in vivo can be drastically modified and result in improved pharmacokinetic properties.

When discovering and developing therapeutic agents, the person skilled in the art attempts to optimise pharmacokinetic parameters while retaining desirable in vitro properties. It is reasonable to assume that many compounds with poor pharmacokinetic profiles are susceptible to oxidative metabolism. In vitro liver microsomal assays currently available provide valuable information on the course of oxidative metabolism of this type, which in turn permits the rational design of deuterated compounds of the formula I with improved stability through resistance to such oxidative metabolism. Significant improvements in the pharmacokinetic profiles of compounds of the formula I are thereby obtained, and can be expressed quantitatively in terms of increases in the in vivo half-life (t1/2), concentration at maximum therapeutic effect ($C_{max}$), area under the dose response curve (AUC), and F; and in terms of reduced clearance, dose and materials costs.

The following is intended to illustrate the above: a compound of the formula I which has multiple potential sites of attack for oxidative metabolism, for example benzylic hydrogen atoms and hydrogen atoms bonded to a nitrogen atom, is prepared as a series of analogues in which various combinations of hydrogen atoms are replaced by deuterium atoms, so that some, most or all of these hydrogen atoms have been replaced by deuterium atoms. Half-life determinations enable favourable and accurate determination of the extent of the extent to which the improvement in resistance to oxidative metabolism has improved. In this way, it is determined that the half-life of the parent compound can be extended by up to 100% as the result of deuterium-hydrogen exchange of this type.

Deuterium-hydrogen exchange in a compound of the formula I can also be used to achieve a favourable modification of the metabolite spectrum of the starting compound in order to diminish or eliminate undesired toxic metabolites. For example, if a toxic metabolite arises through oxidative carbon-hydrogen (C—H) bond cleavage, it can reasonably be assumed that the deuterated analogue will greatly diminish or eliminate production of the unwanted metabolite, even if the particular oxidation is not a rate-determining step. Further information on the state of the art with respect to deuterium-hydrogen exchange may be found, for example in Hanzlik et al., J. Org. Chem. 55, 3992-3997, 1990, Reider et al., J. Org. Chem. 52, 3326-3334, 1987, Foster, Adv. Drug Res. 14, 1-40, 1985, Gillette et al, Biochemistry 33(10) 2927-2937, 1994, and Jarman et al. Carcinogenesis 16(4), 683-688, 1993.

The invention furthermore relates to medicaments comprising at least one compound of the formula I and/or pharmaceutically acceptable salts, solvates and stereoisomers thereof, including mixtures thereof in all ratios, and optionally excipients and/or adjuvants.

Pharmaceutical formulations can be administered in the form of dosage units which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tabletting machine, giving lumps of non-uniform shape, which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a prespecified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula I and pharmaceutically solvates, salts, tautomers and stereoisomers thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the formula I and the solvates. salts, tautomers and stereoisomers thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxy-ethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block co-polymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula I depends on a number of factors, including, for example, the age and weight of the animal, the precise condition that requires treatment, and its severity, the nature of the formulation and the method of administration, and is ultimately determined by the treating doctor or vet. However, an effective amount of a compound according to the invention is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

A combined treatment of this type can be achieved with the aid of simultaneous, consecutive or separate dispensing of the individual components of the treatment. Combination products of this type employ the compounds according to the invention.

The invention furthermore relates to medicaments comprising at least one compound of the formula I and/or pharmaceutically acceptable salts, tautomers and stereoisomers thereof, including mixtures thereof in all ratios, and at least one further medicament active ingredient.

The invention also relates to a set (kit) consisting of separate packs of (a) an effective amount of a compound of the formula I and/or pharmaceutically acceptable salts, tautomers and stereoisomers thereof, including mixtures thereof in all ratios, and (b) an effective amount of a further medicament active ingredient.

The set comprises suitable containers, such as boxes, individual bottles, bags or ampoules. The set may, for example, comprise separate ampoules, each containing an effective amount of a compound of the formula I and/or pharmaceutically acceptable salts, tautomers and stereoisomers thereof, including mixtures thereof in all ratios, and an effective amount of a further medicament active ingredient in dissolved or lyophilised form.

"Treating" as used herein, means an alleviation, in whole or in part, of symptoms associated with a disorder or disease, or slowing, or halting of further progression or worsening of those symptoms, or prevention or prophylaxis of the disease or disorder in a subject at risk for developing the disease or disorder.

The term "effective amount" in connection with a compound of formula (I) can mean an amount capable of alleviating, in whole or in part, symptoms associated with a disorder or disease, or slowing or halting further progression or worsening of those symptoms, or preventing or providing prophylaxis for the disease or disorder in a subject having or at risk for developing a disease disclosed herein, such as inflammatory conditions, immunological conditions, cancer or metabolic conditions.

In one embodiment an effective amount of a compound of formula (I) is an amount that inhibits HIF-2α in a cell, such as, for example, in vitro or in vivo. In some embodiments, the effective amount of the compound of formula (I) inhibits HIF-2α in a cell by 10%, 20%, 30%, 40%, 50%, 60%, 70%, 80%, 90% or 99%, compared to the activity of HIF-2α in an untreated cell. The effective amount of the compound of formula (I), for example in a pharmaceutical composition, may be at a level that will exercise the desired effect; for example, about 0.005 mg/kg of a subject's body weight to about 10 mg/kg of a subject's body weight in unit dosage for both oral and parenteral administration.

USE

The present compounds are suitable as pharmaceutical active ingredients for mammals, especially for humans, in the treatment of cancer.

The present invention encompasses the use of the compounds of the formula I and/or pharmaceutically acceptable salts, tautomers and stereoisomers thereof for the preparation of a medicament for the treatment or prevention of cancer.

Moreover, the present invention encompasses the compounds in formula I and/or pharmaceutically acceptable salts, tautomers and stereoisomers thereof for treatment or prevention of cancer.

Also encompassed is the use of the compounds of the formula I and/or pharmaceutically acceptable solvates, salts, tautomers and stereoisomers thereof for the preparation of a medicament for the treatment or prevention of a HIF-2α-induced disease or a HIF-2α-induced condition in a mammal, in which to this method a therapeutically effective amount of a compound according to the invention is administered to a sick mammal in need of such treatment. The therapeutic amount varies according to the specific disease and can be determined by the person skilled in the art without un-due effort.

The present invention specifically relates to compounds of the formula I and pharmaceutically acceptable salts, solvates. tautomers and stereoisomers thereof, including mixtures thereof in all ratios, for the use for the treatment of diseases in which the inhibition, regulation and/or modulation inhibition of HIF-2α plays a role.

The present invention specifically relates to compounds of the formula I and pharmaceutically acceptable salts, solvates, tautomers and stereoisomers thereof, including mixtures thereof in all ratios, for the use for the inhibition of HIF-2α.

Representative cancers that compounds of formula I are useful for treating or preventing include, but are not limited to, cancer of the head, neck, eye, mouth, throat, esophagus, bronchus, larynx, pharynx, chest, bone, lung, colon, rectum, stomach, prostate, urinary bladder, uterine, cervix, breast, ovaries, testicles or other reproductive organs, skin, thyroid, blood, lymph nodes, kidney, liver, pancreas, brain, central nervous system, solid tumors and blood-borne tumors.

Moreover, representative cancers that compounds of formula I are useful for treating or preventing include glioblastoma, renal cell carcinoma (RCC) and clear cell renal cell carcinoma (ccRCC).

Moreover, the present invention encompasses the compounds for use of the formula I and/or pharmaceutically acceptable salts, tautomers and stereoisomers thereof for treatment or prevention of von Hippel-Lindau (VHL) disease.

Moreover, the present invention encompasses the compounds for use of the formula I and/or pharmaceutically acceptable salts, solvates, tautomers and stereoisomers thereof for treatment or prevention of a cardiovascular disease.

Preferably, the present invention relates to a method of treating cancer comprising administering to a subject in need thereof an effective amount of a compound of formula I according to the invention.

Particularly preferable, the present invention relates to a method wherein the disease is a cancer, wherein administration is simultaneous, sequential or in alternation with administration of at least one other active drug agent.

The disclosed compounds of the formula I can be administered in combination with other known therapeutic agents, including anticancer agents. As used here, the term "anticancer agent" relates to any agent which is administered to a patient with cancer for the purposes of treating the cancer.

The anticancer treatment defined above may be applied as a monotherapy or may involve, in addition to the herein disclosed compounds of formula I, conventional surgery or radiotherapy or medicinal therapy. Such medicinal therapy, e.g. a chemotherapy or a targeted therapy, may include one or more, but preferably one, of the following anti-tumor agents:

Alkylating Agents
- such as altretamine, bendamustine, busulfan, carmustine, chlorambucil, chlormethine, cyclophosphamide, dacarbazine, ifosfamide, improsulfan, tosilate, lomustine, melphalan, mitobronitol, mitolactol, nimustine, ranimustine, temozolomide, thiotepa, treosulfan, mechloretamine, carboquone; apaziquone, fotemustine, glufosfamide, palifosfamide, pipobroman, trofosfamide, uramustine, TH-302[4], VAL-083[4];

Platinum Compounds
- such as carboplatin, cisplatin, eptaplatin, miriplatine hydrate, oxaliplatin, lobaplatin, nedaplatin, picoplatin, satraplatin;

DNA Altering Agents
- such as amrubicin, bisantrene, decitabine, mitoxantrone, procarbazine, trabectedin, clofarabine;
- amsacrine, brostallicin, pixantrone, laromustine[1,3];

Topoisomerase Inhibitors
- such as etoposide, irinotecan, razoxane, sobuzoxane, teniposide, topotecan; amonafide, belotecan, elliptinium acetate, voreloxin;

Microtubule Modifiers
- such as cabazitaxel, docetaxel, eribulin, ixabepilone, paclitaxel, vinblastine, vincristine, vinorelbine, vindesine, vinflunine;
- fosbretabulin, tesetaxel;

Antimetabolites
- such as asparaginase[3], azacitidine, calcium levofolinate, capecitabine, cladribine, cytarabine, enocitabine, floxuridine, fludarabine, fluorouracil, gemcitabine, mercaptopurine, methotrexate, nelarabine, pemetrexed, pralatrexate, azathioprine, thioguanine, carmofur;

doxifluridine, elacytarabine, raltitrexed, sapacitabine, tegafur[2,3], trimetrexate;

Anticancer Antibiotics such as bleomycin, dactinomycin, doxorubicin, epirubicin, idarubicin, levamisole, miltefosine, mitomycin C, romidepsin, streptozocin, valrubicin, zinostatin, zorubicin, daunurobicin, plicamycin;

aclarubicin, peplomycin, pirarubicin;

Hormones/Antagonists such as abarelix, abiraterone, bicalutamide, buserelin, calusterone, chlorotrianisene, degarelix, dexamethasone, estradiol, fluocortolone fluoxymesterone, flutamide, fulvestrant, goserelin, histrelin, leuprorelin, megestrol, mitotane, nafarelin, nandrolone, nilutamide, octreotide, prednisolone, raloxifene, tamoxifen, thyrotropin alfa, toremifene, trilostane, triptorelin, diethylstilbestrol;

acolbifene, danazol, deslorelin, epitiostanol, orteronel, enzalutamide[1,3];

Aromatase Inhibitors such as aminoglutethimide, anastrozole, exemestane, fadrozole, letrozole, testolactone;

formestane;

Small Molecule Kinase Inhibitors such as crizotinib, dasatinib, erlotinib, imatinib, lapatinib, nilotinib, pazopanib, regorafenib, ruxolitinib, sorafenib, sunitinib, vandetanib, vemurafenib, bosutinib, gefitinib, axitinib;

afatinib, alisertib, dabrafenib, dacomitinib, dinaciclib, dovitinib, enzastaurin, nintedanib, lenvatinib, linifanib, linsitinib, masitinib, midostaurin, motesanib, neratinib, orantinib, perifosine, ponatinib, radotinib, rigosertib, tipifarnib, tivantinib, tivozanib, trametinib, pimasertib, brivanib alaninate, cediranib, apatinib[4], cabozantinib S-malate[1,3], ibrutinib[1,3], icotinib[4], buparlisib[2], cipatinib[4], cobimetinib[1,3], idelaisib[1,3], fedratinib[1], XL-647[4];

Photosensitizers such as methoxsalen[3];

porfimer sodium, talaporfin, temoporfin;

Antibodies such as alemtuzumab, besilesomab, brentuximab vedotin, cetuximab, denosumab, ipilimumab, ofatumumab, panitumumab, rituximab, tositumomab, trastuzumab, bevacizumab, pertuzumab[2,3];

catumaxomab, elotuzumab, epratuzumab, farletuzumab, mogamulizumab, necitumumab, nimotuzumab, obinutuzumab, ocaratuzumab, oregovomab, ramucirumab, rilotumumab, siltuximab, tocilizumab, zalutumumab, zanolimumab, matuzumab, dalotuzumab[1,2,3], onartuzumab[1,3], racotumomab[1], tabalumab[1,3], EMD-525797[4], avelumab, nivolumab[1,3];

Cytokines such as aldesleukin, interferon alfa[2], interferon alfa2a[3], interferon alfa2b[2,3]; celmoleukin, tasonermin, teceleukin, oprelvekin[1,3], recombinant interferon beta-1a[4];

Drug Conjugates such as denileukin diftitox, ibritumomab tiuxetan, iobenguane I123, prednimustine, trastuzumab emtansine, estramustine, gemtuzumab, ozogamicin, aflibercept;

cintredekin besudotox, edotreotide, inotuzumab ozogamicin, naptumomab estafenatox, oportuzumab monatox, technetium (99mTc) arcitumomab[1,3], vintafolide[1,3];

Vaccines such as sipuleucel[3]; vitespen[3], emepepimut-S[3], oncoVAX[4], rindopepimut[3], troVax[4], MGN-1601[4], MGN-1703[4];

Miscellaneous alitretinoin, bexarotene, bortezomib, everolimus, ibandronic acid, imiquimod, lenalidomide, lentinan, metirosine, mifamurtide, pamidronic acid, pegaspargase, pentostatin, sipuleucel[3], sizofiran, tamibarotene, temsirolimus, thalidomide, tretinoin, vismodegib, zoledronic acid, vorinostat; celecoxib, cilengitide, entinostat, etanidazole, ganetespib, idronoxil, iniparib, ixazomib, lonidamine, nimorazole, panobinostat, peretinoin, plitidepsin, pomalidomide, procodazol, ridaforolimus, tasquinimod, telotristat, thymalfasin, tirapazamine, tosedostat, trabedersen, ubenimex, valspodar, gendicine[4], picibanil[4], reolysin[4], retaspimycin hydrochloride[1,3], trebananib[2,3], virulizin[4], carfilzomib[1,3], endostatin[4], immucothel[4], belinostat[3], MGN-1703[4];

PARP Inhibitors

Olaparib, Veliparib.

[1] Prop. INN (Proposed International Nonproprietary Name)

[2] Rec. INN (Recommended International Nonproprietary Names)

[3] USAN (United States Adopted Name)

[4] no INN.

The following abbreviations refer respectively to the definitions below:

aq (aqueous), h (hour), g (gram), L (liter), mg (milligram), MHz (Megahertz), min (minute), mm (millimeter), mmol (millimole), mM (millimolar), m.p. (melting point), eq (equivalent), mL (milliliter), μL (microliter), ACN (acetonitrile), AcOH (acetic acid), $CDCl_3$ (deuterated chloroform), $CD_3OD$ (deuterated methanol), C-hex (cyclohexane), DCC (dicyclohexyl carbodiimide), DCM (dichloromethane), DIC (diisopropyl carbodiimide), DIEA (diisopropylethyl-amine), DMF (dimethylformamide), DMSO (dimethylsulfoxide), DMSO-$d_6$ (deuterated dimethylsulfoxide), EDC (1-(3-dimethyl-amino-propyl)-3-ethylcarbodiimide), ESI (Electrospray ionization), EtOAc (ethyl acetate), $Et_2O$ (diethyl ether), EtOH (ethanol), HATU (dimethylamino-([1,2,3]triazolo[4,5-b]pyridin-3-yloxy)-methylene]-dimethyl-ammonium hexafluorophosphate), HPLC (High Performance Liquid Chromatography), i-PrOH (2-propanol), $K_2CO_3$ (potassium carbonate), LC (Liquid Chromatography), MeOH (methanol), $MgSO_4$ (magnesium sulfate), MS (mass spectrometry), MTBE (methyl tert-butyl ether), $NaHCO_3$ (sodium bicarbonate), $NaBH_4$ (sodium borohydride), NMM (N-methyl morpholine), NMR (Nuclear Magnetic Resonance), PE (petroleum ether) PyBOP (benzotriazole-1-yl-oxy-tris-pyrrolidino-phosphonium hexafluorophosphate), RT (room temperature), Rt (retention time), SPE (solid phase extraction), TBTU (2-(1-H-benzotriazole-1-yl)-1,1,3,3-tetramethyluromium tetrafluoro borate), TEA (triethylamine), TFA (trifluoroacetic acid), THF (tetrahydrofuran), TLC (Thin Layer Chromatography), UV (Ultraviolet), WL (wavelength).

Above and below, all temperatures are indicated in ° C. In the following examples, "conventional work-up" means: water is added if necessary, the pH is adjusted, if necessary, to values between 2 and 10, depending on the constitution of the end product, the mixture is extracted with EtOAc or DCM, the phases are separated, the organic phase is dried over sodium sulfate and evaporated, and the residue is purified by chromatography on silica gel and/or by crystallisation. Rf values on silica gel; eluent: EtOAc/MeOH 9:1.

$^{1}H$ NMR was recorded on Bruker DPX-300, DRX-400, AVII-400 or on a 500 MHz spectrometer, using residual signal of deuterated solvent as internal reference. Chemical shifts (δ) are reported in ppm relative to the residual solvent signal (δ=2.49 ppm for $^{1}H$ NMR in DMSO-$d_6$). $^{1}H$ NMR data are reported as follows: chemical shift (multiplicity, coupling constants, and number of hydrogens). Multiplicity is abbreviated as follows: s (singlet), d (doublet), t (triplet), q (quartet), m (multiplet), br (broad).

Analytical Methods

LCMS

Method A

- Column: Ascentis Express C18, 3.0×50 mm, 2.7 μm
- Mobile phase: A: water with 0.05% TFA, B: ACN with 0.05% TFA
- Gradient: 5% B to 100% B till min 2.1, hold till min 2.8 min, 100% B to 5% B till min 2.85, stop after 3.00
- Flow: 1.5 mL/min
- Wave length: 254 nm Method B

- Column: Kinetex EVO C18, 3.0×50 mm, 2.6 μm
- Mobile phase: A: water with 0.04% $NH_4OH$, B: ACN
- Gradient: 10% B to 95% B till min 2.1, hold till min 2.7 min, 95% B to 10% B till min 2.75, stop after 3.00
- Flow: 1.2 mL/min
- Wave length: 254 nm Method C

- Column: Ascentis Express C18, 3.0×50 mm, 2.7 μm
- Mobile phase: A: water with 0.05% TFA, B: ACN with 0.05% TFA
- Gradient: 5% B to 60% B till min 3.0, 60% B to 100% B till min 4.2 min, hold till min 5.2, 100% B to 5% B till min 5.3, stop after 5.60
- Flow: 1.5 mL/min
- Wave length: 254 nm Method D

- Column: Kinetex EVO C18, 3.0×50 mm, 2.6 μm
- Mobile phase: A: water with 0.04% $NH_4OH$, B: ACN
- Gradient: 10% B to 60% B till min 3.0, 60% B to 95% B till min 4.0 min, hold till min 4.8, 95% B to 10% B till min 4.9, stop after 5.20
- Flow: 1.2 mL/min
- Wave length: 254 nm Method E

- Column: Cortecs C18+, 2.1×50 mm, 2.7 μm
- Mobile phase: A: water with 0.1% FA, B: ACN with 0.1% FA
- Gradient: 10% B to 100% B till min 2.0, hold till min 2.6, 100% B to 10% B till min 2.7, stop after 2.90
- Flow: 1.0 mL/min
- Wave length: 254 nm Method F

- Column: Shim-pack GIST C18, 3.0×50 mm, 2.0 μm
- Mobile phase: A: water with 5 mM $NH_4CO_3$, B: ACN
- Gradient: 10% B to 95% B till min 2.1, hold till min 2.7 min, 95% B to 10% B till min 2.75, stop after 3.00
- Flow: 1.2 mL/min
- Wave length: 254 nm Method G

- Column: Durashell C18, 3.0×50 mm, 2.1 μm
- Mobile phase: A: water with 0.04% $NH_4OH$, B: ACN
- Gradient: 10% B to 95% B till min 2.1, hold till min 2.7 min, 95% B to 10% B till min 2.75, stop after 3.00
- Flow: 1.2 mL/min
- Wave length: 254 nm Method H

- Column: Titank C18, 3.0×50 mm, 3.0 μm
- Mobile phase: A: water with 5 mM $NH_4CO_3$, B: ACN
- Gradient: 10% B to 95% B till min 2.1, hold till min 2.7 min, 95% B to 10% B till min 2.75, stop after 3.00
- Flow: 1.2 mL/min
- Wave length: 254 nm Method I

- Column: Poroshell HPH-C18, 3.0×50 mm, 2.7 μm
- Mobile phase: A: water with 0.04% $NH_4OH$, B: ACN
- Gradient: 10% B to 95% B till min 2.1, hold till min 2.7 min, 95% B to 10% B till min 2.75, stop after 3.00
- Flow: 1.2 mL/min
- Wave length: 254 nm Method J

- Column: Cortecs C18+, 2.1×50 mm, 2.7 μm
- Mobile phase: A: water with 0.1% FA, B: ACN with 0.1% FA
- Gradient: 10% B to 60% B till min 3.0, 60% B to 100% B till min 4.0, hold till min 4.7, 100% B to 10% B till min 4.8, stop after 5.00
- Flow: 1.0 mL/min
- Wave length: 254 nm Method K

- Column: Cortecs C18+, 2.1×50 mm, 2.7 μm
- Mobile phase: A: water with 0.1% FA, B: ACN with 0.1% FA
- Gradient: 10% B to 100% B till min 1.10, hold till min 1.60, 100% B to 10% B till min 1.61, stop after 1.90
- Flow: 1.0 mL/min
- Wave length: 254 nm Method L

- Column: Cortecs C18+, 2.1×50 mm, 2.7 μm
- Mobile phase: A: water with 0.1% FA, B: ACN with 0.1% FA
- Gradient: 5% B to 100% B till min 2.0, hold till min 2.6, 100% B to 5% B till min 2.7, stop after 2.90
- Flow: 1.0 mL/min
- Wave length: 254 nm

HPLC

Method A

- Column: XSELECT HSS T3 100×4.6 mm
- Mobile phase: A=Water+0.05% TFA, B=ACN+0.05% TFA
- Gradient: start 5% B, after 8 min 95% B, after 10.2 min 5% B, stop after 12 min
- Flow: 1.2 mL/min
- Wave length: 254 nm Method B

- Column: Ascentis Express C18 2.7 μm, 100×4.6 mm
- Mobile phase: A=Water+0.05% TFA, B=ACN+0.05% TFA
- Gradient: start 5% B, after 8 min 95% B, after 10.2 min 5% B, stop after 12 min
- Flow: 1.5 mL/min
- Wave length: 254 nm Analytical Chiral Separation Method A

- Method: HPLC
- Column: ChiralPak IG-3, 0.46×5 cm, 3 μm
- Mobile phase: Hex(0.1% DEA)/EtOH=7:3
- Wave length: 254 nm
- Flow: 1.0 mL/min Method B Method: HPLC Column: ChiralPak IG-3, 0.46×5 cm, 3 μm Mobile phase: Hex(0.1% DEA)/EtOH=8:2

Wave length: 254 nm

Flow: 1.0 mL/min

Method C

Method: HPLC

Column: ChiralPak IC-3, 0.46×5 cm, 3 μm

Mobile phase: Hex(0.1% DEA)/EtOH=7:3

Wave length: 254 nm

Flow: 1.0 mL/min

Method D

Method: HPLC

Column: ChiralPak IF-3, 0.46×5 cm, 3 μm

Mobile phase: Hex(0.1% DEA)/EtOH=7:3

Wave length: 254 nm

Flow: 1.0 mL/min

Method E

Method: HPLC

Column: ChiralPak IG-3, 0.46×5 cm, 3 μm

Mobile phase: Hex(0.1% DEA)/EtOH=9:1

Wave length: 254 nm

Flow: 1.0 mL/min

Method F

Method: HPLC

Column: ChiralPak IG-3, 0.46×5 cm, 3 μm

Mobile phase: Hex(0.1% DEA)/EtOH=6:4

Wave length: 254 nm

Flow: 1.0 mL/min

Method G

Method: HPLC

Column: ChiralPak IC-3, 0.46×5 cm, 3 μm

Mobile phase: Hex(0.1% DEA)/IPA=1:1

Wave length: 254 nm

Flow: 1.0 mL/min

Method H

Method: HPLC

Column: ChiralPak IF-3, 0.46×5 cm, 3 μm

Mobile phase: Hex(10 mmol $NH_3$)/EtOH=5:5

Wave length: 254 nm

Flow: 1.0 mL/min

Method I

Method: HPLC

Column: Chiral Cellulose-SB, 0.46×10 cm, 3 μm

Mobile phase: Hex(0.1% DEA)/IPA=3:1

Wave length: 254 nm

Flow: 1.0 mL/min

Method J

Method: HPLC

Column: ChiralPak IG-3, 0.46×5 cm, 3 μm

Mobile phase: Hex(0.1% DEA)/EtOH=1:1

Wave length: 254 nm

Flow: 1.0 mL/min

Method K

Method: HPLC

Column: ChiralPak IE-3, 0.46×5 cm, 3 μm

Mobile phase: Hex(0.1% DEA)/EtOH=85:15

Wave length: 254 nm

Flow: 1.0 mL/min

Method L

Method: HPLC

Column: ChiralPak IC-3, 0.46×5 cm, 3 μm

Mobile phase: Hex(0.1% DEA)/IPA=65:35

Wave length: 254 nm

Flow: 1.0 mL/min

Biological Activity

Alphascreen Protein Protein Interaction Assay:

For the assessment of functional disruption of the interaction of the PAS B domains of HIF-2α and HIF-1β an AlphaScreen assay was set-up. The assay was performed in 384 well light gray Perkin Elmer microtiter plates in a total volume of 7 μl. Human rec His6Gb1-TEV-GEFKGL-HIF2α (240-350aa)-G (fc 143 nM) and human rec ARNT His6Gb1-TEV-GEFKGL-ARNT (356-470aa)-FLAG-E362R (fc 143 nM) were incubated with the compound (fc 1 nM to 30 μM) of interest in 20 mM Hepes, 150 mM NaCl, 0.05% Tween 20, 2 mM DTT, 0.1% (w/v) BSA, 0.3% DMSO, pH 7.5 for 15 min at 23° C. The detection of the protein protein interaction was performed by adding AlphaLISA® Anti-FLAG Acceptor beads (fc 20 μg/mL) and AlphaScreen® Nickel Chelate Donor beads (fc 9 μg/mL) (both Perkin Elmer) and the reaction was incubated for 240 min at 23° C. in the dark. If donor and acceptor beads get in close proximity to each other caused by interaction of HIF2alpha PAS B with HIF-1ß PAS B domain it results in a luminescence signal at 615 nm after excitation at 680 nm. The PPI disruption activity of a compound was calculated directly from the loss in Alphascreen signal. The AlphaScreen signal was measured with an Envision multimode reader (Perkin Elmer LAS Germany GmbH). The control value used was the inhibitor-free reaction. The pharmacological zero value used was determined in the absence of HIF-1ß. The inhibitory values (IC50) were calculated using Assay analyser from GeneData.

The compounds inhibit HIF-2α in the assay with an $IC_{50}$ of A<50 nM, 50≤B≤1000 nM, and C>1000 nM as shown in the following table:

| Example | AlphaScreen |
|---|---|
| 1a | A |
| 2a | A |
| 3a | A |
| 4a | A |
| 5a | A |
| 6a | A |
| 7a | A |
| 8a | A |
| 9a | A |
| 10a | A |
| 11a | A |
| 12a | A |
| 13a | A |
| 14a | A |
| 15a | A |
| 16a | A |
| 17a | A |
| 18a | A |
| 19a | A |
| 20a | A |
| 21a | A |
| 22a | A |
| 23a | A |
| 24a | C |
| 25a | B |
| 26a | B |
| 27a | B |
| 28a | B |
| 29a | C |
| 30a | C |
| 31a | C |
| 32a | C |
| 33a | A |
| 34a | B |

ITC

ITC measurements were performed with a VP-ITC microcalorimeter from MicroCal/Malvern (UK). For all titration experiments the protein and the respective compounds were formulated in 30 mM HEPES buffer pH 7.5, 150 mM NaCl and 5 mM ß-mercaptoethanol. The protein, HIF2a (240-350)-G, was prepared by recombinant overexpression and multistep chromatography purification. Compounds were used from concentrated DMSO stock solutions. The final protein concentration in the injection syringe was 100 μM. Ligand stock solutions of 10 mM in DMSO were diluted to 10 μM concentrations with buffer and loaded into the sample cell. All buffers were adjusted to a final concentration of 1% (v/v) DMSO. Both, the titrate and titrant solutions were degassed prior to loading the calorimeter cell and injection syringe. ITC titrations were conducted at a constant temperature of 303 K. ITC data analysis was performed using the Origin 7 (OriginLab Cooperation Northampton, USA)-based calorimetry customization supplied as standard instrument software by MicroCal/Malvern (UK). The integrated heat data were fit with a one-site binding model to determine the apparent values for affinity, enthalpy and stoichiometry of binding.

The compounds bind HIF-2α in the assay with an $K_D$ of A<100 nM, 100≤B≤1000 nM, and C>1000 nM as shown in the following table:

| Example | ITC |
|---|---|
| 1a | B |
| 3a | B |
| 5a | B |
| 7a | A |
| 8a | B |
| 9a | B |
| 12a | B |
| 13a | B |
| 16a | B |
| 19a | A |
| 20a | B |
| 22a | B |
| 24a | C |
| 25a | C |
| 26a | C |
| 27a | B |
| 28a | B |
| 29a | C |
| 30a | C |
| 31a | C |

Cellular Mechanistic Assay: 786-O HRE-luc2P Reporter Assay

This reporter assay was designed to monitor binding of the HIF2α-HIF1β complex to specific DNA fragment called hypoxia response element (HRE) in physiologically relevant cell line. 786-O HRE-luc2P cells were derived from 786-O human renal cell adenocarcinoma cell line by stable integration of a HRE Luc reporter construct (pGL4.42 [luc2P/HRE/Hygro] Vector, Promega, cat no. E4001) driving the expression of luciferase under the control of HRE sequence. HRE is present in promoters of various genes regulated by hypoxia inducible factors. 786-O cells express only HIF2α. As a result, this reporter assay allows monitoring of HIF2α-HIF1β activity by determining the activity of produced luciferase. Cell culture is performed in RPMI media supplemented with 10% FBS, Sodium Pyruvate, Penicillin/Streptomycin, Glutamine, 200 μg/mL Hygromycin Gold.

The assay was performed in 384 well white, opaque microtiterplate with transparent bottom (Greiner Bio-one, Frickenhausen). 786-O HRE-luc2P cells were resuspended at 4×104 cells/mL in fresh, pre-warmed medium (RPMI, 10% FBS, SP, P/S, Q) w/o hygromycin. 50 μl of cell suspension (2000 cells) per well were dispensed in microtiter plates and incubated over night at 37° C. in a 5% $CO_2$ incubator. Compounds were added with Labcyte Echo dispenser (fc 0.3% DMSO, 9 concentrations dilution raw starting at 30 μM). Plates were incubated for 48 h at 37° C. in a 5% $CO_2$ incubator. After this 45 μl of prewarmed ONE-Glo™ EX Reagent were added per well. Plates were placed on an orbital shaker at 1200 rpm for 3 minutes. Plates were sealed and luminescence was measured a Tecan Spark 20M microplate reader (end-point measurement with 0.1 second reading time). Values were normalized to DMSO ctrl and wells without cells (only medium ctrl). Decrease in luminescence directly correlates with inhibition of HIF2α activity. EC50 values and % of effect values were calculated fitting a variable-slope sigmoidal function using Ryvu Therapeutics (formerly Selvita S.A.) DRC application or GraphPad Prism software.

The compounds inhibit HIF-2a in the assay with an IC50 of A<50 nM, 50≤B≤1000 nM, and C>1000 nM as shown in the following table:

| Example | HRE-luc2P reporter assay |
|---|---|
| 1a | B |
| 2a | B |
| 3a | B |
| 4a | B |
| 5a | B |
| 6a | A |
| 7a | B |
| 8a | B |
| 9a | C |
| 10a | C |
| 11a | B |
| 12a | B |
| 13a | C |
| 14a | B |
| 15a | B |
| 16a | C |
| 17a | B |
| 18a | B |
| 19a | B |
| 20a | B |
| 21a | B |
| 23a | C |
| 24a | C |
| 25a | C |
| 26a | C |
| 27a | C |
| 28a | C |
| 29a | C |
| 30a | C |
| 31a | C |
| 32a | C |
| 33a | B |
| 34a | C |

Synthesis

General Procedure

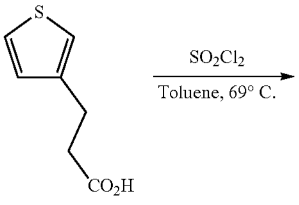

32

-continued
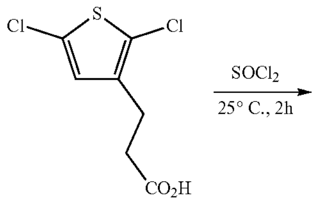
33
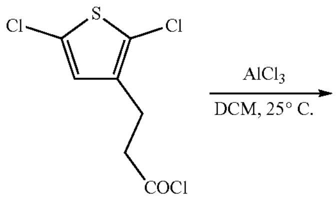
34
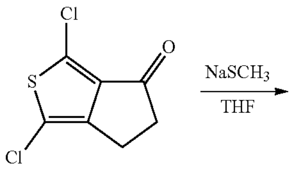
35
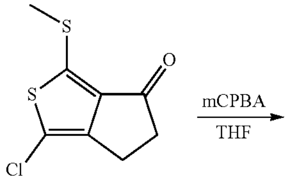
36
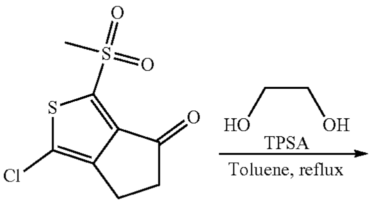
37
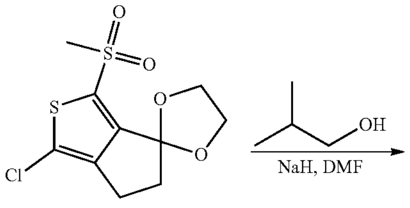
38
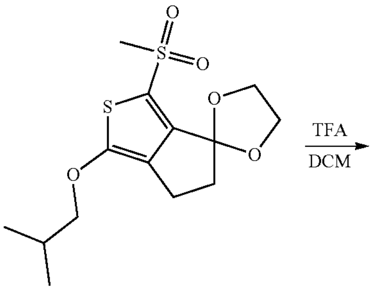
39
-continued
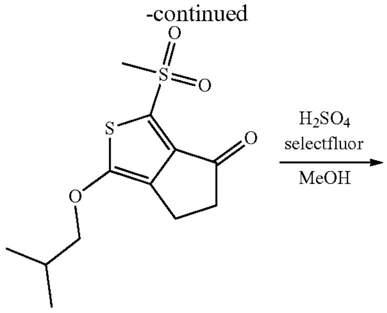
40
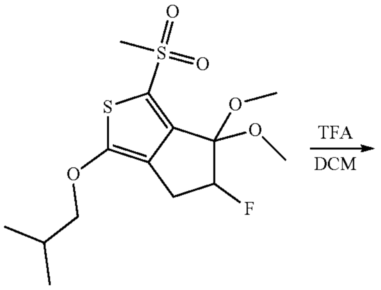
41
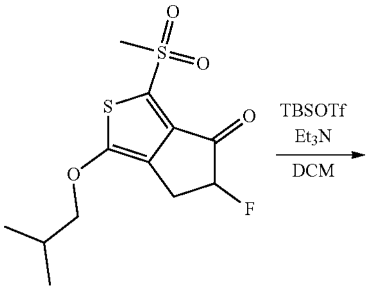
42
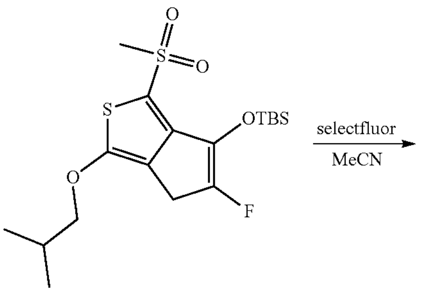
43
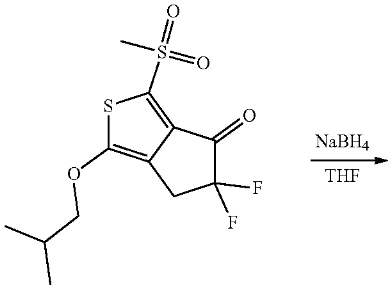
44

-continued

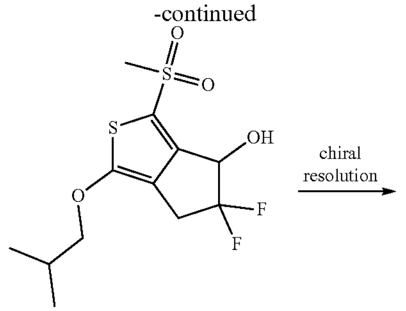

8

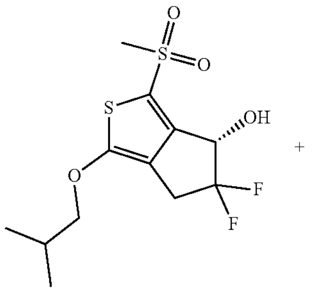

8a

+

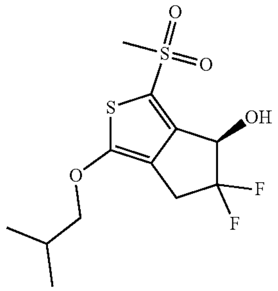

8b

Synthesis of 3-(2,5-dichlorothiophen-3-yl)propanoic acid (2)

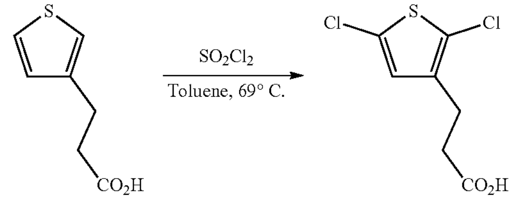

32 33

To 3-(thiophen-3-yl)propanoic acid (6.00 g, 36.49 mmol, 95%) in a 250 mL round-bottom flask was added toluene (70 mL) and $SO_2Cl_2$ (11.92 g, 83.90 mmol, 95%). The resulting solution was stirred at 69° C. for 4 h. The reaction was then quenched by the addition of 100 mL of water/ice and extracted with 4×100 mL of EtOAc. The combined organic layer was dried over sodium sulfate, filtered and the solvent evaporated. The residue was purified via column chromatography eluting with 0-8% EtOAc in PE to afford 8.89 g of 3-(2,5-dichlorothiophen-3-yl)propanoic acid as a colorless solid.

$^1$H NMR (400 MHz, DMSO-$d_6$): δ 12.00 (s, 1H), 7.07 (s, 1H), 2.75-2.70 (m, 2H), 2.54-2.48 (m, 2H); LC-MS (method D): $[M-H]^-$=222.75, Rt=0.89 min.

Synthesis of 3-(2,5-dichlorothiophen-3-yl)propanoyl chloride (3)

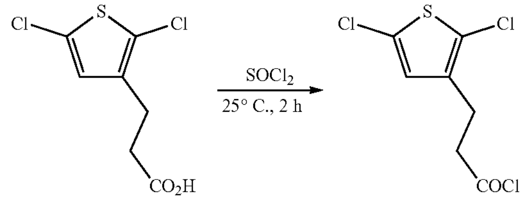

33 34

To 3-(2,5-dichlorothiophen-3-yl)propanoic acid (8.89 g, 36.89 mmol, 93.4%) in a 250 mL round-bottom flask purged with nitrogen was added thionyl chloride (80.00 mL, 1.05 mol, 95%). The resulting solution was stirred at 25° C. for 3 h. The mixture was then concentrated under reduced pressure to afford 8.32 g of 3-(2,5-dichlorothiophen-3-yl) propanoyl chloride as orange oil which was used without further purification.

Synthesis of 1,3-dichloro-5H,6H-cyclopenta[c]thiophen-4-one (4)

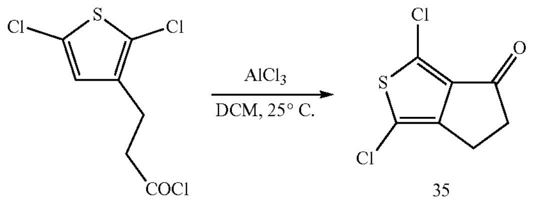

34 35

3-(2,5-dichlorothiophen-3-yl)propanoyl chloride (8.32 g, 32.04 mmol, 93.8%) was dissolved in DCM (80 mL) in a 500 mL round-bottom flask purged with nitrogen and the solution was cooled to 0-5° C. $AlCl_3$ (35.98 g, 256.3 mmol, 95%) was added slowly. The resulting mixture was stirred at 25° C. for 5 h. It was then poured into 1 L of water/ice and extracted with 3×300 mL of EtOAc. The combined organic layer was dried over sodium sulfate, filtered and the solvent evaporated. The residue was purified via column chromatography eluting with EtOAc (0-10%) in PE to afford 4.02 g 1,3-dichloro-5H,6H-cyclopenta[c]thiophen-4-one as a light yellow solid.

$^1$H NMR (400 MHz, $CDCl_3$): δ 3.01-2.95 (m, 2H), 2.87-2.81 (m, 2H); LC-MS (Method D): $[M+H]^+$=206.80, Rt=0.95 min.

Synthesis of 1-chloro-3-(methylsulfanyl)-4H,5H,6H-cyclopenta[c]thiophen-4-one

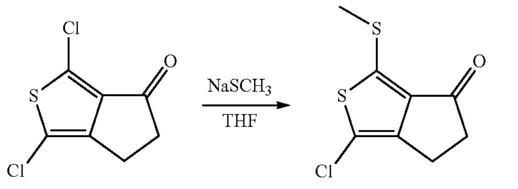

35 36

Into a 250-mL round-bottom flask purged with nitrogen, was placed 1,3-dichloro-5H,6H-cyclopenta[c]thiophen-4-one (4.57 g, 21.10 mmol), tetrahydrofuran (97 mL) and (methylsulfanyl)sodium (1.77 g, 23.99 mmol). The resulting solution was stirred for 4 h at 25° C. The reaction was then quenched by the addition of $H_2O$. The resulting solution was extracted with 100 mL of ethyl acetate. The organic layer was dried, filtered and the solvent evaporated. The residue was applied onto a silica gel column with ethyl acetate/petroleum ether (1:20) to gain 3.3 g (71%) of 1-chloro-3-(methylsulfanyl)-4H,5H,6H-cyclopenta[c]thiophen-4-one as a red solid. LC-MS (Method K): $[M+H]^+$=218.85, Rt=0.92 min.

Synthesis of 1-chloro-3-methanesulfonyl-4H,5H,6H-cyclopenta[c]thiophen-4-one

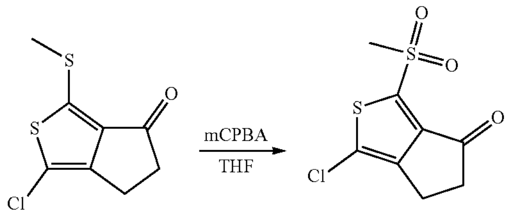

36 37

Into a 50-mL round-bottom flask purged and maintained with an inert atmosphere of nitrogen, was placed 1-chloro-3-(methylsulfanyl)-4H,5H,6H-cyclopenta[c]thiophen-4-one (3.3 g, 15.0 mmol), dichloromethane (31 mL) and m-CPBA (17.2 g, 74.75 mmol, 75%). The resulting solution was stirred for 2 h at 25° C. and quenched with water. The resulting solution was extracted with 4×50 mL of ethyl acetate and the organic layers combined, dried over sodium sulfate, filtered and concentrated under vacuum to afford 3.3 g (85%) of 1-chloro-3-methanesulfonyl-4H,5H,6H-cyclopenta[c]thiophen-4-one as white solid. LC-MS (Method K): $[M+H]^+$=250.85, Rt=0.71 min.

Synthesis of 1-chloro-3-methanesulfonyl-5,6-dihydrospiro[cyclopenta[c]thiophene-4,2'[1,3]dioxolane]

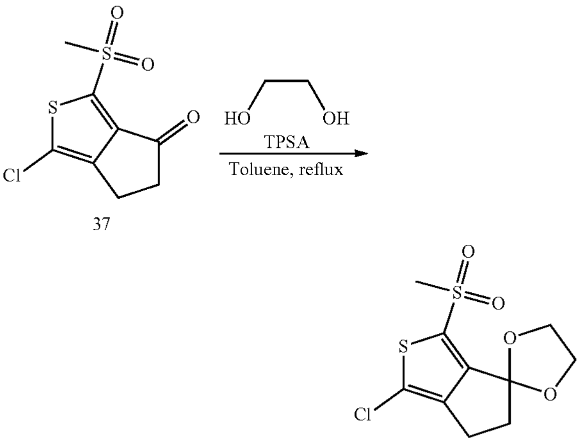

37

38

Into a 250-mL round-bottom flask purged with nitrogen, was placed 1-chloro-3-methanesulfonyl-4H,5H,6H-cyclopenta[c]thiophen-4-one (3.00 g, 10.0 mmol), ethane-1,2-diol (1.30 g, 20.0 mmol), TsOH (0.36 g, 1.996 mmol), toluene (100 mL). The resulting solution was stirred for 16 h at 125° C. The resulting mixture was concentrated and the residue purified via column chromatography (ethyl acetate:petroleum ether=1:3). This resulted in 2.8 g (94%) of 1-chloro-3-methanesulfonyl-5,6-dihydrospiro[cyclopenta[c]thiophene-4,2'-[1,3]dioxolane] as a yellow solid. LC-MS (Method K): $[M+H]^+$=294.95, Rt=0.94 min.

Synthesis of 3-methanesulfonyl-1-(2-methylpropoxy)-5,6-dihydrospiro[cyclopenta[c]thiophene-4,2'-[1,3]dioxolane]

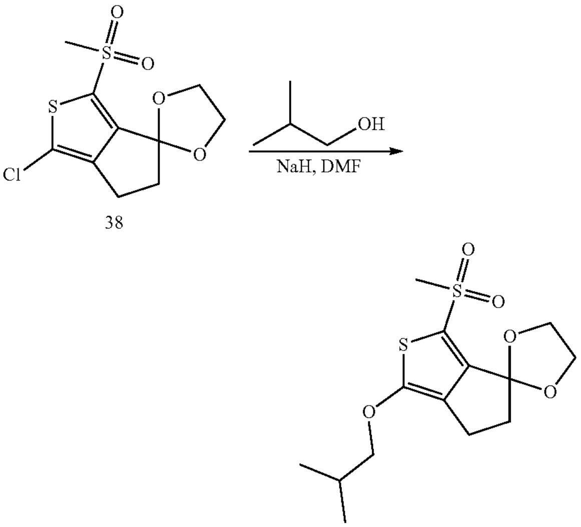

38

39

Into a 20-mL vial purged nitrogen, was placed 2-methylpropan-1-ol (1286 mg, 16.5 mmol), DMF (20 mL). This was followed by the addition of potassium isobutoxide (1.04 g, 8.8 mmol). The mixture was stirred for 20 min at 0° C. To this was added 1-chloro-3-methanesulfonyl-5,6-dihydrospiro[cyclopenta[c]thiophene-4,2'[1,3]dioxolane] (900 mg, 2.75 mmol), 15-crown-5 (955.71 mg, 4.1 mmol). The resulting solution was stirred for 3 h at 55° C. in an oil bath, cooled to room temperature and quenched with water. The resulting solution was extracted with 3×50 mL of ethyl acetate and the organic layers combined, filtered and concentrated under vacuum. The residue was applied onto a silica gel column with ethyl acetate/petroleum ether (1:4). This resulted in 566 mg (53%) of 3-methanesulfonyl-1-(2-methylpropoxy)-5,6-dihydrospiro[cyclopenta[c]thiophene-4,2'[1,3]dioxolane] as a brown solid. LC-MS (Method K): $[M+H]^+$=333.05, Rt=1.06 min.

Synthesis of 3-methanesulfonyl-1-(2-methylpropoxy)-4H,5H,6H-cyclopenta[c]thiophen-4-one

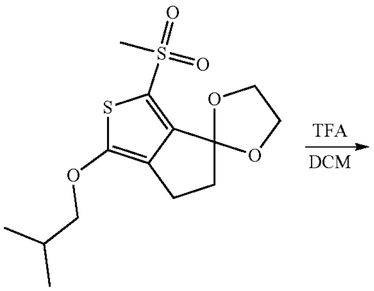

39

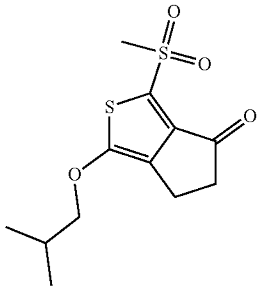

40

Into a 100-mL round-bottom flask was placed 3-methanesulfonyl-1-(2-methylpropoxy)-5,6-dihydrospiro[cyclopenta[c]thiophene-4,2-[1,3]dioxolane] (556 mg, 1.5 mmol), DCM (10 mL) and TFA (1.5 mL, 19.2 mmol). The resulting solution was stirred for 3 h at 25° C. The reaction was then quenched by the addition of 30 mL of $NaHCO_3$. The resulting solution was extracted with ethyl acetate, the combined organic layer was dried over sodium sulfate, filtered and concentrated under vacuum. This resulted in 500 mg (74.9% pure, 86%) of 3-methanesulfonyl-1-(2-methylpropoxy)-4H,5H,6H-cyclopenta[c]thiophen-4-one as a brown solid. LC-MS (Method K): $[M+H]^+$=288.95, Rt=0.94 min.

Synthesis of 5-fluoro-3-methanesulfonyl-4,4-dimethoxy-1-(2-methylpropoxy)-4H,5H,6H-cyclopenta[c]thiophene

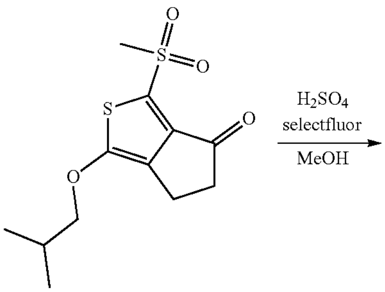

40

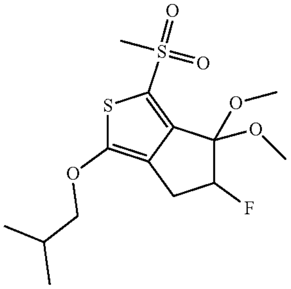

41

Into a 20-mL vial purged and maintained with an inert atmosphere of nitrogen, was placed 3-methanesulfonyl-1-(2-methylpropoxy)-4H,5H,6H-cyclopenta[c]thiophen-4-one (560 mg, 1.45 mmol, 74.9%), MeOH (10 mL), selectfluor (1376 mg, 3.7 mmol), $H_2SO_4$ (0.25 mL, 4.5 mmol). The resulting solution was stirred for 3 h at 60° C. in an oil bath. The resulting solution was extracted with 3×30 mL ethyl acetate and the organic layers were combined, filtered and concentrated under vacuum. This resulted in 550 mg (39% pure, 42%) of 5-fluoro-3-methanesulfonyl-4,4-dimethoxy-1-(2-methylpropoxy)-4H,5H,6H-cyclopenta[c]thiophene as a brown solid. LC-MS (Method K): $[M+H—CH_3—OCH_3]^+$=306.95, Rt=1.09 min.

Synthesis of 5-fluoro-3-methanesulfonyl-1-(2-methylpropoxy)-4H,5H,6H-cyclopenta[c]thiophen-4-one

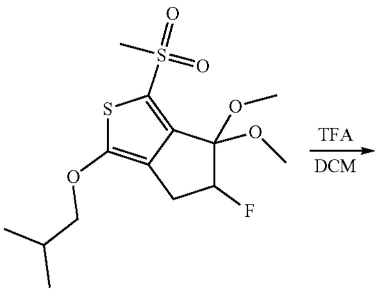

41

-continued

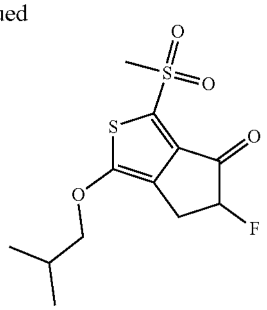

42

Into a 100-mL round-bottom flask, was placed 5-fluoro-3-methanesulfonyl-4,4-dimethoxy-1-(2-methylpropoxy)-4H,5H,6H-cyclopenta[c]thiophene (550 mg, 0.858 mmol, 39%), DCM (10 mL), TFA (2 mL, 25.580 mmol). The resulting solution was stirred for 2 h at 25° C. The reaction was then quenched by the addition of water. The resulting mixture was extracted with 3×20 mL of ethyl acetate and the organic layers combined, filtered and concentrated under vacuum. This resulted in 520 mg (45% pure, 89%) of 5-fluoro-3-methanesulfonyl-1-(2-methylpropoxy)-4H,5H,6H-cyclopenta[c]thiophen-4-one as a solid. LC-MS (Method K): $[M+H]^+$=306.95, Rt=1.10 min.

Synthesis of tert-butyl({[5-fluoro-1-methanesulfonyl-3-(2-methylpropoxy)-4H-cyclopenta[c]thiophen-6-yl]oxy})dimethylsilane

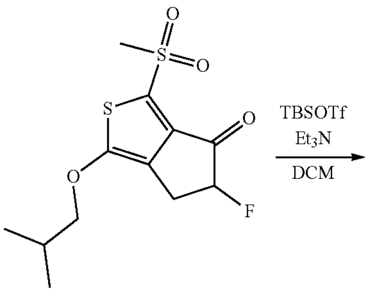

42

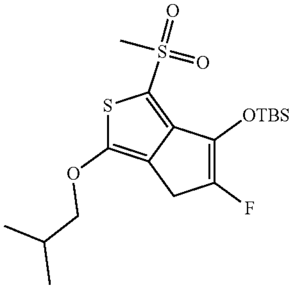

43

Into a 50-mL 3-necked round-bottom flask purged with nitrogen, was placed 5-fluoro-3-methanesulfonyl-1-(2-methylpropoxy)-4H,5H,6H-cyclopenta[c]thiophen-4-one (100 mg, 0.29 mmol), DCM (5 mL), TEA (160 mg, 1.50 mmol, 95%), TBSOTf (252 mg, 0.91 mmol). The resulting mixture was stirred for 3 h at room temperature and then concentrated under vacuum. The residue was purified via column chromatography (ethyl acetate:petroleum ether=1:5). This resulted in 100 mg (74%) of tert-butyl({[5-fluoro-1-methanesulfonyl-3-(2-methylpropoxy)-4H-cyclopenta[c]thiophen-6-yl]oxy})dimethylsilane as yellow oil. LC-MS (Method K): $[M+H]^+$=421.10, Rt=1.36 min.

Synthesis of 5,5-difluoro-3-methanesulfonyl-1-(2-methylpropoxy)-4H,5H,6H-cyclopenta[c]thiophen-4-one

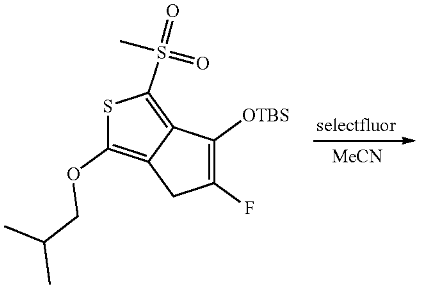

43

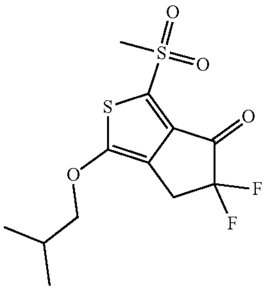

44

Into a 25-mL round-bottom flask, was placed tert-butyl({[5-fluoro-1-methanesulfonyl-3-(2-methylpropoxy)-4H-cyclopenta[c]thiophen-6-yl]oxy})dimethylsilane (90 mg, 0.19 mmol), MeCN (4 mL), selectfluor (151.5 mg, 0.41 mmol). The resulting solution was stirred for 2 h at room temperature. The resulting solution was diluted with 50 mL of ethyl acetate. The resulting mixture was washed with 2×30 mL of aqueous NaCl, dried over anhydrous sodium sulfate, filtered and concentrated under vacuum. This resulted in 60 mg (86%) of 5,5-difluoro-3-methanesulfonyl-1-(2-methylpropoxy)-4H,5H,6H-cyclopenta[c]thiophen-4-one as a yellow solid. LC-MS (Method K): $[M+H]^+$=325.05, Rt=0.97 min.

Synthesis of 5,5-difluoro-3-methanesulfonyl-1-(2-methylpropoxy)-4H,5H,6H-cyclopenta[c]thiophen-4-ol

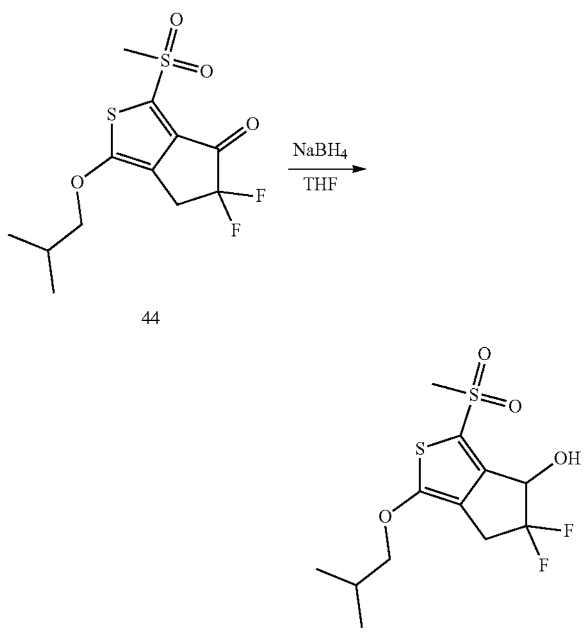

44

8

Into a 25-mL round-bottom flask, was placed 5,5-difluoro-3-methanesulfonyl-1-(2-methylpropoxy)-4H,5H,6H-cyclopenta[c]thiophen-4-one (30 mg, 0.08 mmol), THF (4 mL), $NaBH_4$ (7.0 mg, 0.18 mmol). The resulting solution was stirred for 2 h at room temperature and diluted with 30 mL of ethyl acetate. The resulting mixture was washed with 2×20 mL of aqueous NaCl, dried over anhydrous sodium sulfate, filtered and concentrated. 5,5-difluoro-3-methanesulfonyl-1-(2-methylpropoxy)-4H,5H,6H-cyclopenta[c]thiophen-4-ol was obtained as a white solid.

Chiral resolution of 5,5-difluoro-3-methanesulfonyl-1-(2-methylpropoxy)-4H,5H,6H-cyclopenta[c]thiophen-4-ol (8)

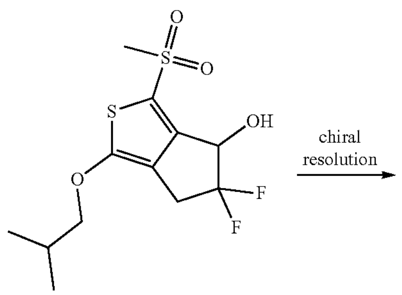

8

-continued

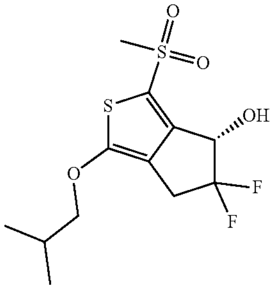

+

8a

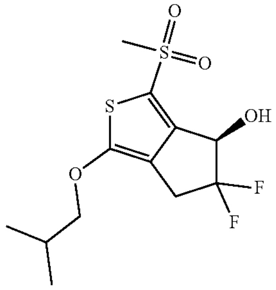

8b 5,5-difluoro-3-methanesulfonyl-1-(2-methylpropoxy)-4H,5H,6H-cyclopenta[c]thiophen-4-ol (8) were separated by Chiral-Prep-HPLC under the following condition: HPLC Column: ChiralPak IG-3, 0.46×5 cm, 3 μm mobile phase: Hex(0.1% DEA)/EtOH=9:1, wave length: 254 nm, flow: 1.0 mL/min. This resulted in 30.3 mg of (4S)-5,5-difluoro-3-methanesulfonyl-1-(2-methylpropoxy)-4H,5H,6H-cyclopenta[c]thiophen-4-ol (8a) as a white solid with a melting point of 65-68° C.

8a: $^1H$ NMR (300 MHz, $CD_3OD$): δ=5.04 (dd, J=11.6, 2.8 Hz, 1H), 3.97 (d, J=6.5 Hz, 2H), 3.25 (s, 3H), 3.24-3.12 (m, 2H), 2.18-2.00 (m, 1H), 1.03 (d, J=6.7 Hz, 6H); LC-MS (method E): Rt=1.24 min, $[M+HCOO]^-$=370.75; HPLC (method B): purity 99.1%, Rt 5.28 min; chiral HPLC (method E): 98.0% er, Rt 3.95 min, (8b: Rt=3.53 min).

Following compounds have been obtained analogously:

(4S)-1-(cyclohexyloxy)-5,5-difluoro-3-methanesulfonyl-4H,5H,6H-cyclopenta[c]thiophen-4-ol (1a)

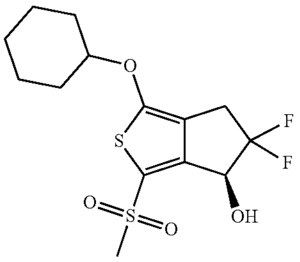 [SMILES: CS(=O)(=O)c1sc(OC2CCCCC2)c2c1[C@H](O)C(F)(F)C2]

Prepared according to general procedure; $^1H$ NMR (300 MHz, $CD_3OD$): δ=5.06-5.02 (m, 1H), 4.31-4.23 (m, 1H), 3.27 (s, 3H), 3.21-3.08 (m, 2H), 2.06 (m, 2H), 1.80-1.74 (m, 2H), 1.66-1.58 (m, 3H), 1.52-1.35 (m, 3H); LC-MS (method A): Rt=1.47 min, $[M+Na]^+$=274.9; HPLC (method A): purity 99.7%, Rt 6.70 min; chiral HPLC (method A): >99.5% ee, Rt 2.2 min.

The (4R)-enantiomer has been obtained analogously.

(4S)-1-(2,2-dimethylpropoxy)-5,5-difluoro-3-methanesulfonyl-4H,5H,6H-cyclopenta[c]thiophen-4-ol (2a)

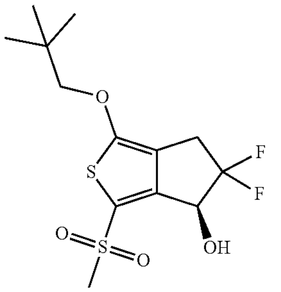 [SMILES: CC(C)(C)COc1sc(S(C)(=O)=O)c2c1CC(F)(F)[C@H]2O]

Prepared according to general procedure; $^1$H NMR (300 MHz, $CD_3OD$): δ=5.06 (dd, J=11.5, 2.9 Hz, 1H), 3.88 (s, 2H), 3.28 (s, 3H), 3.23 (ddd, J=16.2, 9.0, 5.4 Hz, 2H), 1.06 (s, 9H); LC-MS (method B): Rt=1.66 min, $[M+NH_4]^+$ =358.1; HPLC (method B): purity 98.6%, Rt 5.72 min; chiral HPLC (method B): >99.5% ee, Rt 1.53 min.

The (4R)-enantiomer has been obtained analogously.

(4S)-1-cyclobutoxy-5,5-difluoro-3-methanesulfonyl-4H,5H,6H-cyclopenta[c]thiophen-4-ol (3a)

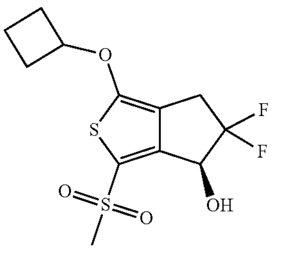 [SMILES: CS(=O)(=O)c1sc(OC2CCC2)c2c1[C@H](O)C(F)(F)C2]

Prepared according to general procedure; $^1$H NMR (300 MHz, $CD_3OD$): δ=5.06-5.02 (m, 1H), 4.80-4.73 (m, 1H), 3.26-3.14 (m, 5H), 2.55-2.45 (m, 2H), 2.31-2.18 (m, 2H), 1.95-1.85 (m, 1H), 1.78-1.68 (m, 1H); LC-MS (method A): Rt=1.52 min, $[M+Na]^+$=346.9; HPLC (method A): purity 99.5%, Rt 6.0 min; chiral HPLC (method B): 99.8% er, Rt 2.26 min.

The (4R)-enantiomer has been obtained analogously.

(4S)-5,5-difluoro-3-methanesulfonyl-1-(2-methylbutoxy)-4H,5H,6H-cyclopenta[c]thiophen-4-ol (4a)

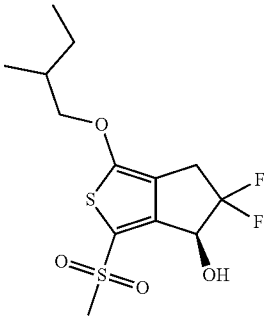 [SMILES: CCC(C)COc1sc(S(C)(=O)=O)c2c1CC(F)(F)[C@H]2O]

Prepared according to general procedure; $^1$H NMR (300 MHz, $CD_3OD$): δ=5.06 (dd, J=11.4, 2.7 Hz, 1H), 4.08-3.96 (m, 2H), 3.31 (s, 3H), 3.22-3.14 (m, 2H), 1.94-1.83 (m, 1H), 1.62-1.48 (m, 1H), 1.36-1.21 (m, 1H), 1.03-0.93 (m, 6H); LC-MS (method C): Rt=2.75 min, $[M+Na]^+$=363.0; HPLC (method A): purity 97.4%, Rt 6.75 min; chiral HPLC (method C): >99.5% ee, Rt 1.24 min.

The (4R)-enantiomer has been obtained analogously.

(4S)-1-(2,2-difluoroethoxy)-5,5-difluoro-3-methanesulfonyl-4H,5H,6H-cyclopenta[c]thiophen-4-ol (5a)

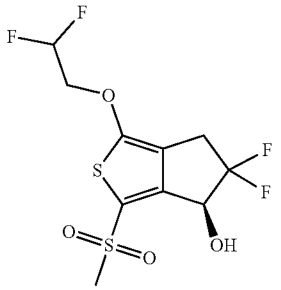 [SMILES: CS(=O)(=O)c1sc(OCC(F)F)c2c1[C@H](O)C(F)(F)C2]

Prepared according to general procedure; $^1$H NMR (300 MHz, DMSO-$d_6$): δ=6.69 (m, 1H), 6.56-6.21 (m, 1H), 4.97 (m, 1H), 4.62-4.52 (m, 2H), 3.44-3.28 (m, 5H); LC-MS (method A): Rt=1.06 min, $[M+Na]^+$=356.8; HPLC (method A): purity 99.9%, Rt 5.16 min; chiral HPLC (method A): 99.5% ee, Rt 1.9 min.

The (4R)-enantiomer has been obtained analogously.

(4S)-5,5-difluoro-3-methanesulfonyl-1-(3,3,3-trifluoro-2-methylpropoxy)-4H,5H,6H-cyclopenta[c]thiophen-4-ol (6a)

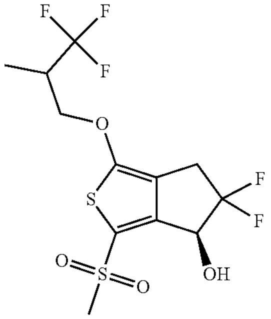 [SMILES: CC(COc1sc(S(C)(=O)=O)c2c1CC(F)(F)[C@H]2O)C(F)(F)F]

Prepared according to general procedure; $^1$H NMR (300 MHz, DMSO-$d_6$): δ=6.69 (d, J=7.1 Hz, 1H), 5.03-4.87 (m, 1H), 4.34 (d, J=5.4 Hz, 2H), 3.28 (d, J=5.6 Hz, 5H), 2.97 (d, J=7.6 Hz, 1H), 1.18 (d, J=7.1 Hz, 3H); LC-MS (method D): Rt=2.52 min, $[M+NH_4]^+$=398.1; HPLC (method A): purity 99.5%, Rt 6.20 min; chiral HPLC (method B): >99.5% ee, Rt 2.13 min.

The (4R)-stereoisomers have been obtained analogously.

(4S)-5,5-difluoro-3-methanesulfonyl-1-(2,2,2-trifluoroethoxy)-4H,5H,6H-cyclopenta[c]thiophen-4-ol (7a)

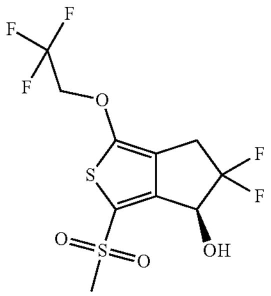 [SMILES: CS(=O)(=O)c1sc(OCC(F)(F)F)c2c1[C@H](O)C(F)(F)C2]

Prepared according to general procedure; $^1$H NMR (300 MHz, DMSO-$d_6$): δ=5.08 (d, J=6.9 Hz, 1H), 5.07-4.99 (m, 3H), 3.40-3.35 (m, 5H); LC-MS (method E): Rt=1.14 min, $[M+HCOO]^-$=396.7; HPLC (method A): purity 99.6%, Rt 5.6 min; chiral HPLC (method D): >99.5% ee, Rt 1.22 min.

The (4R)-enantiomer has been obtained analogously.

(4S)-5,5-difluoro-3-methanesulfonyl-1-(2-methylpropoxy)-4H,5H,6H-cyclopenta[c]thiophen-4-ol (8a)

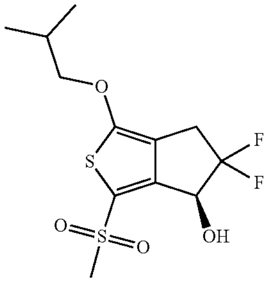 [SMILES: CC(C)COc1sc(S(C)(=O)=O)c2c1CC(F)(F)[C@H]2O]

Prepared according to general procedure; $^1$H NMR (300 MHz, $CD_3OD$): δ=5.04 (dd, J=11.6, 2.8 Hz, 1H), 3.97 (d, J=6.5 Hz, 2H), 3.25 (s, 3H), 3.24-3.12 (m, 2H), 2.18-2.00 (m, 1H), 1.03 (d, J=6.7 Hz, 6H); LC-MS (method E): Rt=1.24 min, $[M+HCOO]^-$=370.75; HPLC (method B): purity 99.1%, Rt 5.28 min; chiral HPLC (method E): 98.0% er, Rt 3.95 min.

The (4R)-enantiomer has been obtained analogously.

(4S)-5,5-difluoro-3-methanesulfonyl-1-{[1,1,1-trifluorobutan-2-yl]oxy}-4H,5H,6H-cyclopenta[c]thiophen-4-ol (9a)

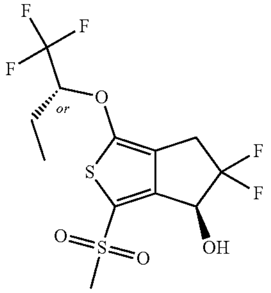 [SMILES: CC[C@@H](Oc1sc(S(C)(=O)=O)c2c1CC(F)(F)[C@H]2O)C(F)(F)F]

Prepared according to general procedure; $^1$H NMR (400 MHz, $CD_3OD$): δ=5.08 (dd, J=11.1, 3.0 Hz, 1H), 4.74-4.65 (m, 1H), 3.28 (s, 3H), 3.26-3.18 (m, 2H), 2.01-1.83 (m, 2H), 1.13 (t, J=7.6 Hz, 3H); LC-MS (method E): Rt=1.44 min, $[M+HCOO]^-$=424.75; HPLC (method B): purity 99.6%, Rt 5.44 min; chiral HPLC (method B): 99.8% er, Rt 2.36 min.

In the formula "or" means unknown configuration.

The stereoisomers have been obtained analogously.

(4S)-{[1,1-difluoropropan-2-yl]oxy}-5,5-difluoro-3-methanesulfonyl-4H,5H,6H-cyclopenta[c]thiophen-4-ol (10a)

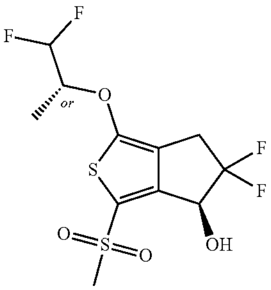 [SMILES: C[C@@H](Oc1sc(S(C)(=O)=O)c2c1CC(F)(F)[C@H]2O)C(F)F]

Prepared according to general procedure; $^1$H NMR (300 MHz, $CD_3OD$): δ=6.18-5.81 (m, 1H), 5.08-5.03 (m, 1H), 4.62-4.47 (m, 1H), 3.29-3.14 (m, 5H), 1.45 (s, 3H); LC-MS (method D): Rt=2.14 min, $[M+NH_4]^+$=366.0; HPLC (method B): purity 96.5%, Rt 4.50 min; chiral HPLC (method A): >99.5% ee, Rt 2.17 min.

In the formula "or" means unknown configuration.

The stereoisomers have been obtained analogously.

(4S)-5,5-difluoro-3-methanesulfonyl-1-(3,3,3-trifluoropropoxy)-4H,5H,6H-cyclopenta[c]thiophen-4-ol (11a)

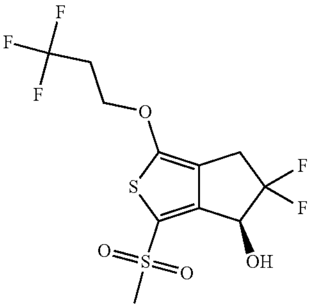 [SMILES: CS(=O)(=O)c1sc(OCCC(F)(F)F)c2c1[C@H](O)C(F)(F)C2]

Prepared according to general procedure; $^1$H NMR (300 MHz, $CD_3OD$): δ=5.07 (dd, J=11.5, 3.0 Hz, 1H), 4.44 (t, J=5.8 Hz, 2H), 3.29 (s, 3H), 3.26-3.19 (m, 2H), 2.86-2.71 (m, 2H); LC-MS (method B): Rt=1.41 min, $[M+NH_4]^+$=384.0; HPLC (method A): purity 96.1%, Rt 4.74 min; chiral HPLC (method B): >99.5%, Rt 1.61 min.

The (4R)-enantiomer has been obtained analogously.

(4S)-5,5-difluoro-3-methanesulfonyl-1-propoxy-4H,5H,6H-cyclopenta[c]thiophen-4-ol (12a)

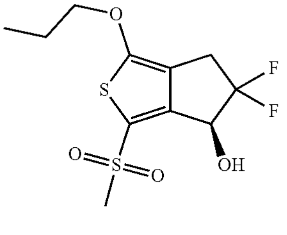 [SMILES: CCCOc1sc(S(C)(=O)=O)c2c1CC(F)(F)[C@H]2O]

Prepared according to general procedure; $^1$H NMR (300 MHz, $CD_3OD$): δ=5.08 (m, 2H), 4.19-4.15 (m, 2H), 3.25-3.11 (m, 5H), 1.91-1.80 (m, 2H), 1.08-1.06 (m, 3H); LC-MS (method F): Rt=1.77 min, $[M-H]^-$=311.0; HPLC (method A): purity 98.9%, Rt 5.91 min; chiral HPLC (method F): >99.5% ee, Rt 1.10 min.

The (4R)-enantiomer has been obtained analogously.

(4S)-1-(cyclopropylmethoxy)-5,5-difluoro-3-methanesulfonyl-4H,5H,6H-cyclopenta[c]thiophen-4-ol (13a)

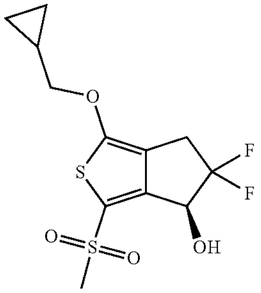 [SMILES: CS(=O)(=O)c1sc(OCC2CC2)c2c1[C@H](O)C(F)(F)C2]

Prepared according to general procedure; $^1$H NMR (300 MHz, $CD_3OD$): δ=5.08 (dd, J=11.1, 3.0 Hz, 1H), 4.05 (d, J=7.2 Hz, 2H), 3.27-3.15 (m, 5H), 1.39-1.26 (m, 1H), 0.71-0.60 (m, 2H), 0.45-0.39 (m, 2H); LC-MS (method G): Rt=1.41 min, $[M+NH_4]^+$=342.1; HPLC (method A): purity 99.8%, Rt 5.79 min; chiral HPLC (method B): >99.5% ee, Rt 5.45 min.

The (4R)-enantiomer has been obtained analogously.

(4S)-1-{[1,1-difluoropropan-2-yl]oxy}-5,5-difluoro-3-methanesulfonyl-4H,5H,6H-cyclopenta[c]thiophen-4-ol (14a)

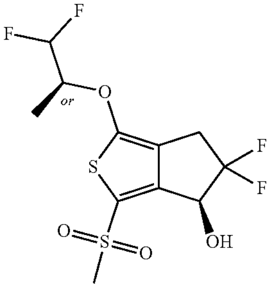 [SMILES: C[C@H](Oc1sc(S(C)(=O)=O)c2c1CC(F)(F)[C@H]2O)C(F)F]

Prepared according to general procedure; $^1$H NMR (300 MHz, $CD_3OD$): δ=6.19-5.81 (m, 1H), 5.08-5.03 (m, 1H), 4.62-4.47 (m, 1H), 3.30-3.14 (m, 5H), 1.44 (s, 3H); LC-MS (method D): Rt=2.14 min, $[M+NH_4]^+$=366.1; HPLC (method B): purity 96.8%, Rt 4.52 min; chiral HPLC (method A): >99.5% ee, Rt 1.74 min.

In the formula "or" means unknown configuration.

The stereoisomers have been obtained analogously.

(4S)-1-(2,2-difluoropropoxy)-5,5-difluoro-3-methanesulfonyl-4H,5H,6H-cyclopenta[c]thiophen-4-ol (15a)

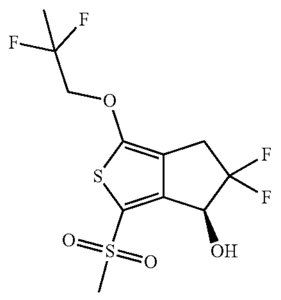 [SMILES: CC(F)(F)COc1sc(S(C)(=O)=O)c2c1CC(F)(F)[C@H]2O]

Prepared according to general procedure; $^1$H NMR (400 MHz, $CDCl_3$): 5.24 (dd, J=11.5, 4.8 Hz, 1H), 4.28-4.20 (t, J=11.2 Hz, 2H), 3.40-3.14 (m, 6H), 1.78 (t, J=18.8 Hz, 3H); LC-MS (method H): Rt=1.62 min, $[M-H]^-$=346.9; HPLC (method B): purity 99.5%, Rt 4.7 min; chiral HPLC (method A): >99.5% ee, Rt 2.21 min.

The (4R)-enantiomer has been obtained analogously.

(4S)-5,5-difluoro-3-methanesulfonyl-1-[(1-methoxycyclobutyl)methoxy]-4H,5H,6H-cyclopenta[c]thiophen-4-ol (16a)

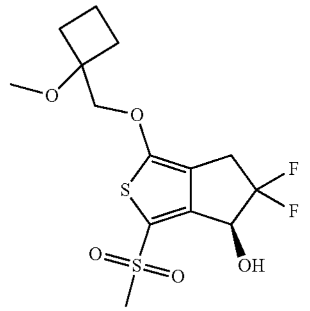 [SMILES: COC1(COc2sc(S(C)(=O)=O)c3c2CC(F)(F)[C@H]3O)CCC1]

Prepared according to general procedure; $^1$H NMR (300 MHz, $CD_3OD$): δ=5.08 (dd, J=11.4, 2.7 Hz, 1H), 4.33 (s, 2H), 3.36-3.30 (m, 4H), 3.28-3.17 (m, 4H), 2.30-2.19 (m, 2H), 2.11-2.03 (m, 2H), 1.90-1.67 (m, 2H); LC-MS (method E): Rt=1.09 min, $[M+COO]^-$=412.8; HPLC (method A): purity 99.8%, Rt 5.71 min; chiral HPLC (method A): >99.5% ee, Rt 1.55 min.

The (4R)-enantiomer has been obtained analogously.

(4S,5S)-5-fluoro-3-methanesulfonyl-1-(2,2,2-trifluoroethoxy)-4H,5H,6H-cyclopenta[c]thiophen-4-ol (17a)

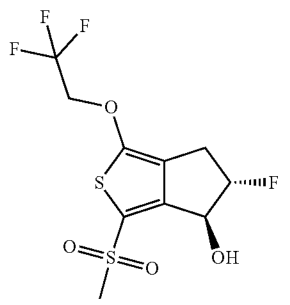 [SMILES: CS(=O)(=O)c1sc(OCC(F)(F)F)c2c1[C@H](O)[C@@H](F)C2]

Prepared according to general procedure; $^1$H NMR (400 MHz, $CD_3OD$): δ=5.39-5.19 (m, 2H), 4.79-4.73 (m, 2H), 3.37-3.32 (m, 3H), 3.15-3.03 (m, 2H); LC-MS (method B): Rt=1.24 min, $[M-H]^-$=332.9; HPLC (method B): purity 98.0%, Rt 4.08 min; chiral HPLC (method A): >99.5% ee, Rt 3.67 min.

The stereoisomers have been obtained analogously.

(4S)-1-[(3,3-difluorocyclobutyl)methoxy]-5,5-difluoro-3-methanesulfonyl-4H,5H,6H-cyclopenta[c]thiophen-4-ol (18a)

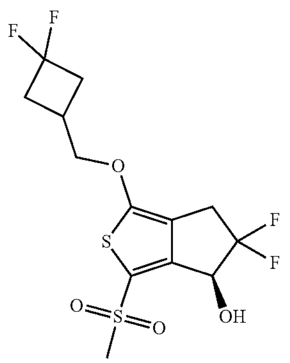 [SMILES: CS(=O)(=O)c1sc(OCC2CC(F)(F)C2)c2c1[C@H](O)C(F)(F)C2]

Prepared according to general procedure; $^1$H NMR (300 MHz, DMSO-$d_6$): δ=6.68 (d, J=7.0 Hz, 1H), 5.06-4.88 (m, 1H), 4.28 (d, J=6.0 Hz, 2H), 3.29 (d, J=16.1 Hz, 5H), 2.83-2.57 (m, 3H), 2.49 (s, 2H); LC-MS (method B): Rt=1.49 min, $[M+NH_4]^+$=392.1; HPLC (method B): purity 99.5%, Rt 4.98 min; chiral HPLC (method A): >99.5% ee, Rt 1.42 min.

The (4R)-enantiomer has been obtained analogously.

(4S)-1-(cyclobutylmethoxy)-5,5-difluoro-3-methanesulfonyl-4H,5H,6H-cyclopenta[c]thiophen-4-ol (19a)

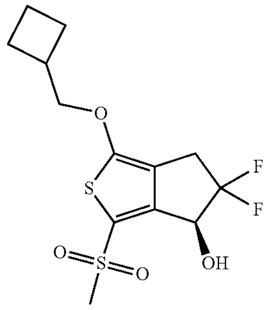 [SMILES: CS(=O)(=O)c1sc(OCC2CCC2)c2c1[C@H](O)C(F)(F)C2]

Prepared according to general procedure; $^{1}$H NMR (300 MHz, $CD_3OD$): δ=5.08 (dd, J=2.7 Hz, 1H), 4.18 (d, J=6.3 Hz, 2H), 3.27 (s, 3H), 3.24-3.16 (m, 2H), 2.88-2.78 (m, 1H), 2.21-2.09 (m, 2H), 2.06-1.80 (m, 4H); LC-MS (method E): Rt=1.28 min, $[M+Na]^+$=362.0; HPLC (method A): purity 99.8%, Rt 6.47 min; chiral HPLC (method A): >99.5% ee, Rt 2.20 min.

The (4R)-enantiomer has been obtained analogously.

(4S)-1-(1-cyclobutylethoxy)-5,5-difluoro-3-methanesulfonyl-4H,5H,6H-cyclopenta[c]thiophen-4-ol (20a)

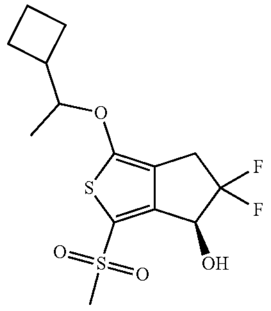 [SMILES: CC(Oc1sc(S(C)(=O)=O)c2c1CC(F)(F)[C@H]2O)C1CCC1]

Prepared according to general procedure; $^{1}$H NMR (300 MHz, $CD_3OD$): δ=5.08 (dd, J=11.7, 2.7 Hz, 1H), 4.31-4.23 (m, 1H), 3.29-3.06 (m, 5H), 2.64-2.51 (m, 1H), 2.07-1.77 (m, 6H), 1.28 (d, J=6 Hz, 3H); LC-MS (method E): Rt=1.41 min, $[2M+H]^+$=705.1; HPLC (method A): purity 99.4%, Rt 6.78 min; chiral HPLC (method B): 99.2% er, Rt 1.45 min.

The stereoisomers have been obtained analogously.

(4S)-1-(3,3-difluorobutoxy)-5,5-difluoro-3-methanesulfonyl-4H,5H,6H-cyclopenta[c]thiophen-4-ol (21a)

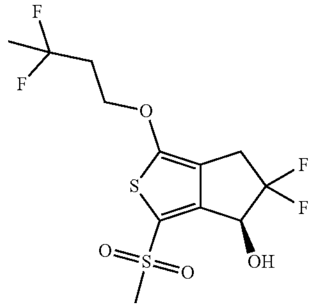 [SMILES: CC(F)(F)CCOc1sc(S(C)(=O)=O)c2c1CC(F)(F)[C@H]2O]

Prepared according to general procedure; $^{1}$H NMR (300 MHz, DMSO-$d_6$): δ=6.71 (d, J=7.0 Hz, 1H), 5.06-4.92 (m, 1H), 4.43-4.32 (m, 2H), 3.34 (s, 3H), 3.31-3.19 (m, 2H), 2.49-2.36 (m, 2H), 1.76-1.61 (m, 3H); LC-MS (method H): Rt=2.86 min, $[M+NH_4]^+$=380.0; HPLC (method B): purity 97.4%, Rt 4.71 min; chiral HPLC (method A): >99.5% ee, Rt 1.25 min.

The (4R)-enantiomer has been obtained analogously.

(4S)-5,5-difluoro-3-methanesulfonyl-1-(oxan-4-yloxy)-4H,5H,6H-cyclopenta[c]thiophen-4-ol (22a)

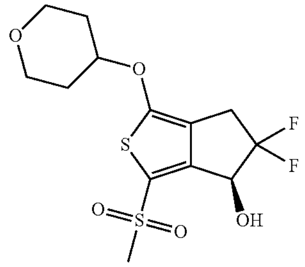 [SMILES: CS(=O)(=O)c1sc(OC2CCOCC2)c2c1[C@H](O)C(F)(F)C2]

Prepared according to general procedure; $^{1}$H NMR (300 MHz, $CD_3OD$): δ=5.08-5.04 (m, 1H), 4.55-4.47 (m, 1H), 3.99-3.91 (m, 2H), 3.63-3.55 (m, 2H), 3.32-3.14 (m, 5H), 2.14-2.08 (m, 2H), 1.86-1.75 (m, 2H); LC-MS (method F): Rt=1.35 min, $[M+Na]^+$=376.9; HPLC (method A): purity 99.9%, Rt 4.96 min; chiral HPLC (method G): >99.5% ee, Rt 2.07 min.

The (4R)-enantiomer has been obtained analogously.

(4S)-5,5-difluoro-3-methanesulfonyl-1-[2-(trifluoromethoxy)ethoxy]-4H,5H,6H-cyclopenta[c]thiophen-4-ol (23a)

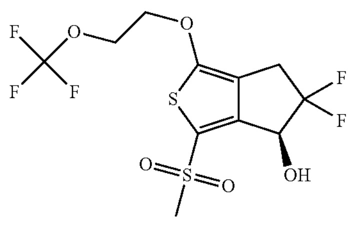 [SMILES: CS(=O)(=O)c1sc(OCCOC(F)(F)F)c2c1[C@H](O)C(F)(F)C2]

Prepared according to general procedure; $^1$H NMR (400 MHz, $CD_3OD$): δ=5.07 (dd, J=11.4, 3.0 Hz, 1H), 4.48-4.42 (m, 2H), 4.42-4.35 (m, 2H), 3.29 (s, 3H), 3.36-3.15 (m, 2H); LC-MS (method B): Rt=2.42 min, $[M+NH_4]^+$=400.0; HPLC (method B): purity 99.0%, Rt 4.90 min; chiral HPLC (method E): >99.5% ee, Rt 2.71 min.

The (4R)-enantiomer has been obtained analogously.

1-(3,4-difluorophenoxy)-5,5-difluoro-3-methanesulfonyl-4H,5H,6H-cyclopenta[c]thiophen-4-ol (24a)

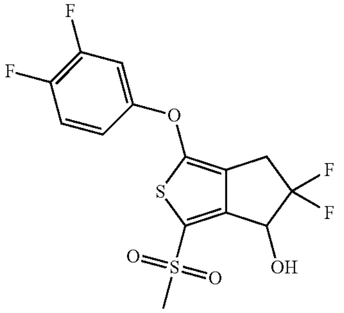 [SMILES: CS(=O)(=O)c1sc(Oc2ccc(F)c(F)c2)c2c1C(O)C(F)(F)C2]

Prepared according to general procedure; $^1$H NMR (300 MHz, $CDCl_3$): δ=7.23-7.17 (m, 1H), 7.05-6.98 (m, 1H), 6.93-6.87 (m, 1H), 5.27-5.21 (m, 1H), 3.49 (s, 1H), 3.26 (s, 3H), 3.19-2.96 (m, 2H); LC-MS (method E): Rt=1.24 min, $[M+H]^+$=404.9; HPLC (method A): purity 99.3%, Rt 6.44 min; racemic.

(4S)-5,5-difluoro-3-methanesulfonyl-1-(propan-2-yloxy)-4H,5H,6H-cyclopenta[c]thiophen-4-ol (25a)

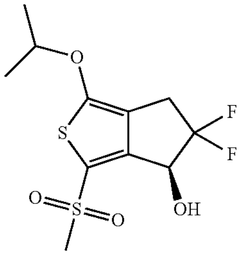 [SMILES: CC(C)Oc1sc(S(C)(=O)=O)c2c1CC(F)(F)[C@H]2O]

Prepared according to general procedure; $^1$H NMR (300 MHz, $CD_3OD$): δ=5.05 (m, 1H), 4.53 (m, 1H), 3.28-3.25 (s, 3H), 3.24-3.13 (m, 2H), 1.42 (d, 6H); LC-MS (method I): Rt=1.37 min, $[M+NH_4]^+$=330.0; HPLC (method B): purity 99.8%, Rt 4.4 min; chiral HPLC (method G): >99.5% ee, Rt 1.38 min.

The (4R)-enantiomer has been obtained analogously.

3-chloro-5-{[(4S)-5,5-difluoro-4-hydroxy-3-methanesulfonyl-4H,5H,6H-cyclopenta[c]thiophen-1-yl]oxy}benzonitrile (26a)

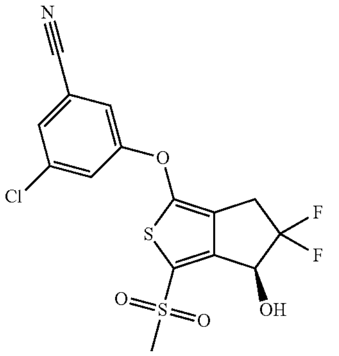 [SMILES: CS(=O)(=O)c1sc(Oc2cc(Cl)cc(C#N)c2)c2c1[C@H](O)C(F)(F)C2]

Prepared according to general procedure; $^1$H NMR (300 MHz, $CD_3OD$): δ=7.69 (t, 1H), 7.59-7.54 (m, 2H), 5.14 (m, 1H), 3.34 (s, 3H), 3.11 (m, 2H); LC-MS (method E): Rt=1.29 min, $[M+Na]^+$=429.0; HPLC (method A): purity 99.9%, Rt 6.45 min; chiral HPLC (method G): >99.5% ee, Rt 1.70 min.

The (4R)-enantiomer has been obtained analogously.

(4S)-1-(3,5-difluorophenoxy)-5,5-difluoro-3-methanesulfonyl-4H,5H,6H-cyclopenta[c]thiophen-4-ol (27a)

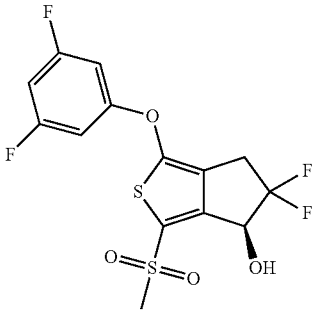 [SMILES: CS(=O)(=O)c1sc(Oc2cc(F)cc(F)c2)c2c1[C@H](O)C(F)(F)C2]

Prepared according to general procedure; $^1$H NMR (300 MHz, $CD_3OD$): δ=7.00-6.73 (m, 3H), 5.15 (dd, J=11.2, 3.2 Hz, 1H), 3.35 (s, 3H), 3.23-2.95 (m, 2H); LC-MS (method I): Rt=1.61 min, $[M+NH_4]^+$=400.2; HPLC (method A): purity 9.74%, Rt 6.5 min; chiral HPLC (method H): >99.5% ee, Rt 1.35 min.

The (4R)-enantiomer has been obtained analogously.

3-{[(4S)-5,5-difluoro-4-hydroxy-3-methanesulfonyl-4H,5H,6H-cyclopenta[c]thiophen-1-yl]oxy}-5-fluorobenzonitrile (28a)

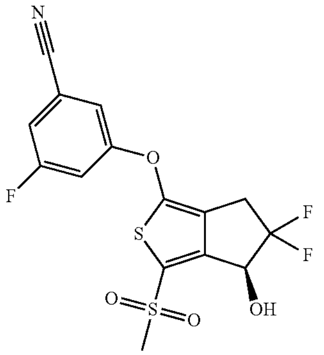 [SMILES: CS(=O)(=O)c1sc(Oc2cc(F)cc(C#N)c2)c2c1[C@H](O)C(F)(F)C2]

Prepared according to general procedure; $^1$H NMR (300 MHz, $CD_3OD$): δ=7.52-7.42 (m, 2H), 7.38 (m, 1H), 5.16 (m, 1H), 3.36 (s, 3H), 3.13 (m, 2H); LC-MS (method I): Rt=1.50 min, $[M-H]^-$=367.9; HPLC (method A): purity 99.1%, Rt 6.09 min; chiral HPLC (method A): >99.5% ee, Rt 2.87 min.

The (4R)-enantiomer has been obtained analogously.

(4S)-5,5-difluoro-1-(4-fluorophenoxy)-3-methanesulfonyl-4H,5H,6H-cyclopenta[c]thiophen-4-ol (29a)

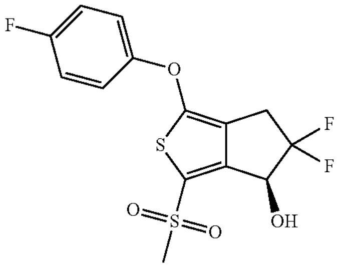 [SMILES: CS(=O)(=O)c1sc(Oc2ccc(F)cc2)c2c1[C@H](O)C(F)(F)C2]

Prepared according to general procedure; $^1$H NMR (400 MHz, $CD_3OD$): δ=7.36-7.09 (m, 4H), 5.10 (dd, J=11.3, 3.1 Hz, 1H), 3.30 (s, 3H), 3.19-2.87 (m, 2H); LC-MS (method B): Rt=1.55 min, $[M+NH_4]^+$=382.2; HPLC (method A): purity 99.7%, Rt 6.29 min; chiral HPLC (method C): >99.5% ee, Rt 1.53 min.

The (4R)-enantiomer has been obtained analogously.

(4S)-1-(3-chloro-5-fluorophenoxy)-5,5-difluoro-3-methanesulfonyl-4H,5H,6H-cyclopenta[c]thiophen-4-ol (30a)

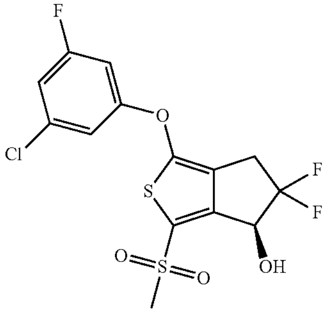 [SMILES: CS(=O)(=O)c1sc(Oc2cc(F)cc(Cl)c2)c2c1[C@H](O)C(F)(F)C2]

Prepared according to general procedure; $^1$H NMR (300 MHz, $CD_3OD$): δ=7.19-7.09 (m, 2H), 7.00 (m, 1H), 5.16 (m, 1H), 3.36 (s, 3H), 3.12 (m, 2H); LC-MS (method J): Rt=2.71 min, $[M+Na]^+$=420.8; HPLC (method A): purity 99.4%, Rt 7.26 min; chiral HPLC (method I): >99.5% ee, Rt 2.31 min.

The (4R)-enantiomer has been obtained analogously.

3-{[(4S)-5,5-difluoro-4-hydroxy-3-methanesulfonyl-4H,5H,6H-cyclopenta[c]thiophen-1-yl]oxy}benzonitrile (31a)

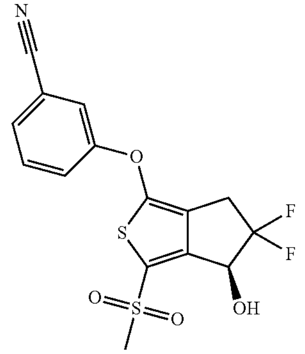 [SMILES: CS(=O)(=O)c1sc(Oc2cccc(C#N)c2)c2c1[C@H](O)C(F)(F)C2]

Prepared according to general procedure; $^1$H NMR (300 MHz, $CD_3OD$): δ=7.67-7.58 (m, 3H), 7.53 (m, 1H), 5.14 (dd, 1H), 3.14 (d, 3H), 3.12-3.00 (m, 2H); LC-MS (method E): Rt=1.16 min, $[M+H]^+$=371.9; HPLC (method A): purity 98.7%, Rt 5.90 min; chiral HPLC (method J): >99.5% ee, Rt 1.35 min.

The (4R)-enantiomer has been obtained analogously.

(4S)-1-ethoxy-5,5-difluoro-3-methanesulfonyl-4H,5H,6H-cyclopenta[c]thiophen-4-ol (32a)

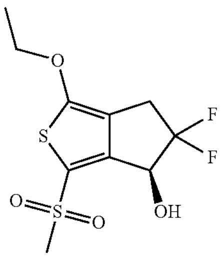 [SMILES: CCOc1sc(S(C)(=O)=O)c2c1CC(F)(F)[C@H]2O]

Prepared according to general procedure; $^1$H NMR (300 MHz, $CD_3OD$): δ=5.05 (dd, J=11.4, 2.7 Hz, 1H), 4.27-4.20 (m, 2H), 3.31 (s, 3H), 3.22-3.14 (m, 2H), 1.43 (t, J=6.9 Hz, 3H), LC-MS (method L): Rt=1.05 min, $[M+H]^+$=299.00; HPLC (method B): purity 99.2%, Rt 4.15 min; chiral HPLC (method L): >99.5% ee, Rt 1.30 min.

The (4R)-enantiomer has been obtained analogously.

(4S)-5,5-difluoro-3-methanesulfonyl-1-(4,4,4-trifluorobutoxy)-4H,5H,6H-cyclopenta[c]thiophen-4-ol (33a)

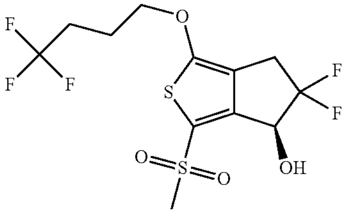 [SMILES: CS(=O)(=O)c1sc(OCCCC(F)(F)F)c2c1[C@H](O)C(F)(F)C2]

Prepared according to general procedure; $^1$H NMR (300 MHz, DMSO-$d_6$): δ=6.68 (d, J=7.2 Hz, 1H), 4.97-4.95 (m, 1H), 4.26 (t, J=6.3 Hz, 2H), 3.29-3.22 (m, 5H), 2.44-2.38 (m, 2H), 1.99-1.93 (m, 2H); LC-MS (method D): Rt=2.63 min, $[M+NH_4]^+$=398.1; HPLC (method B): purity 99.5%, Rt 5.18 min; chiral HPLC (method K): >99.5% ee, Rt 2.31 min.

The (4R)-stereoisomer has been obtained analogously.

(4S)-1-(3,4-difluorophenoxy)-5,5-difluoro-3-methanesulfonyl-4H,5H,6H-cyclopenta[c]thiophen-4-ol (34a)

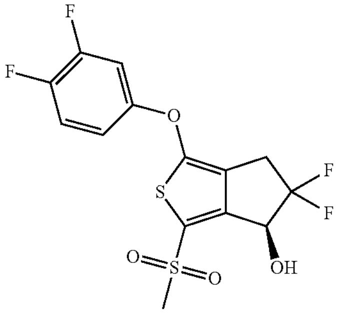 [SMILES: CS(=O)(=O)c1sc(Oc2ccc(F)c(F)c2)c2c1[C@H](O)C(F)(F)C2]

Prepared according to general procedure; $^1$H NMR (300 MHz, $CDCl_3$): δ=7.23-7.17 (m, 1H), 7.05-6.98 (m, 1H), 6.93-6.87 (m, 1H), 5.27-5.21 (m, 1H), 3.49 (s, 1H), 3.26 (s, 3H), 3.19-2.96 (m, 2H); LC-MS (method E): Rt=1.24 min, $[M+H]^+$=404.85; HPLC (method A): purity 99.3%, Rt 6.44 min.

The (4R)-stereoisomer has been obtained analogously.

The following compounds can be prepared in an analogous manner:

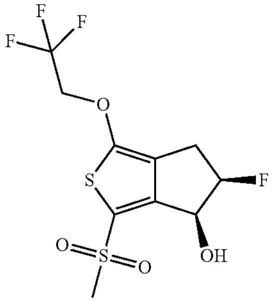
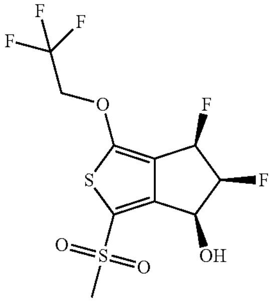
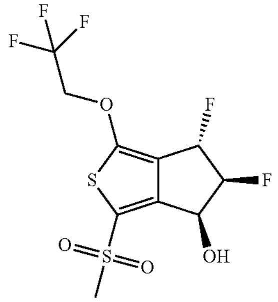
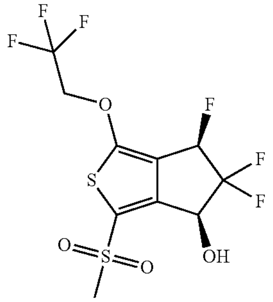
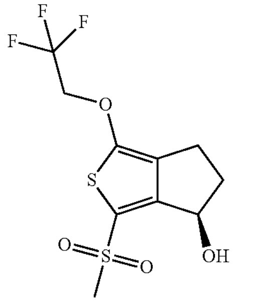
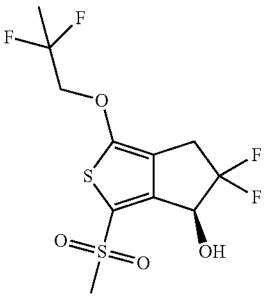
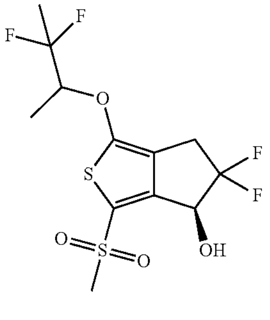
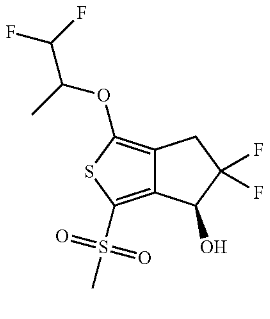

-continued
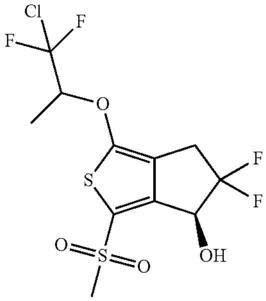
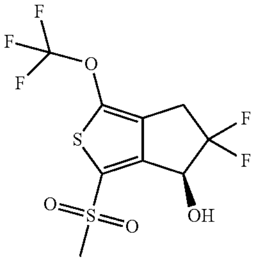
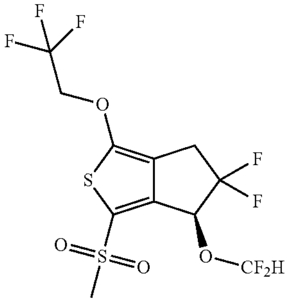
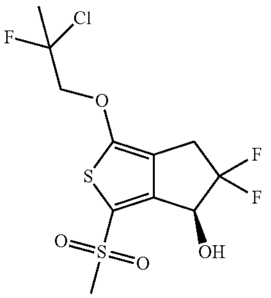
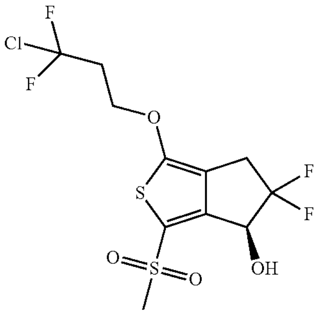
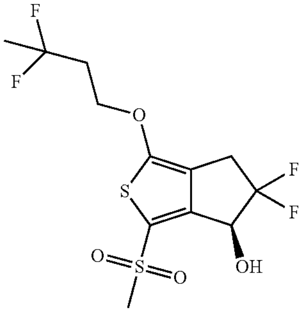
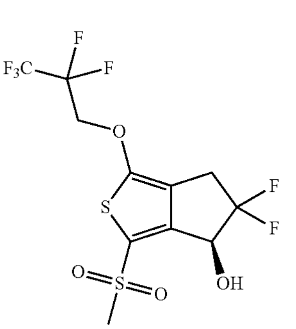
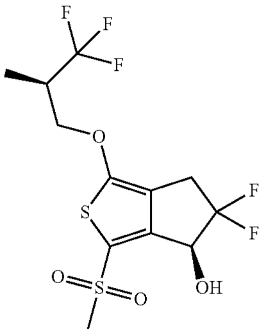
-continued
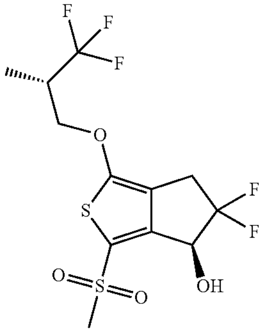
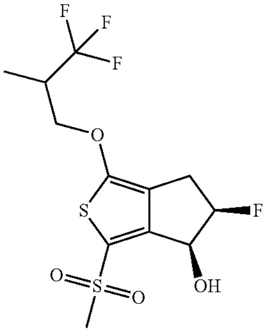
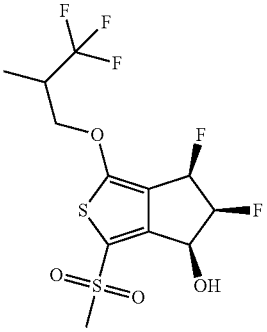
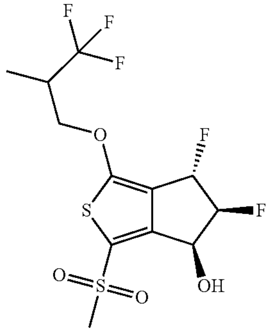
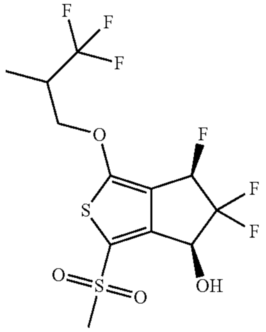
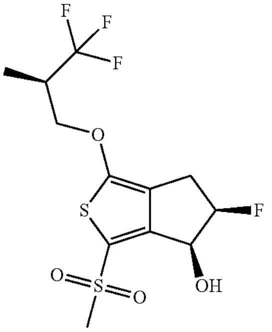
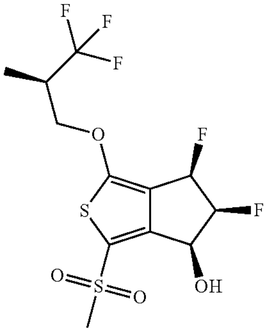
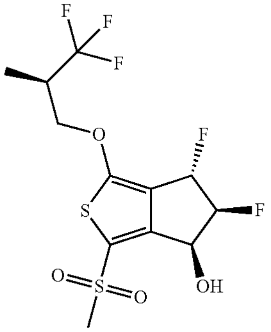
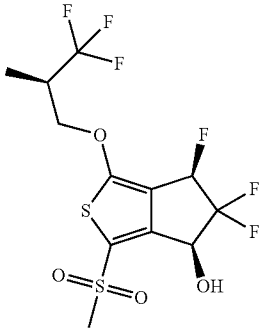
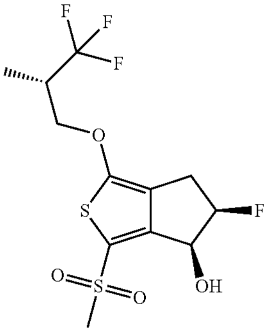

-continued

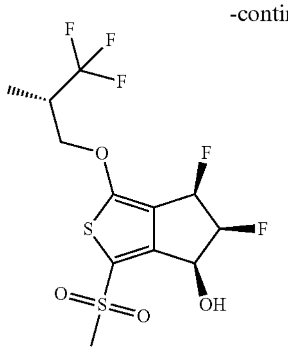

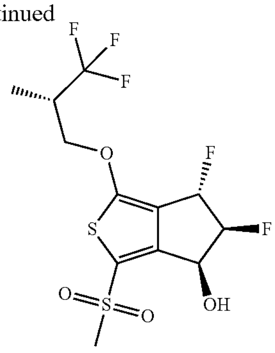

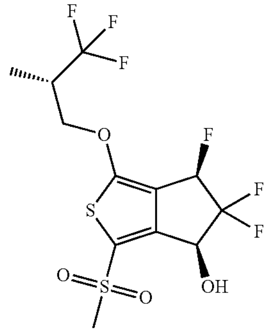 [SMILES: C[C@@H](COc1sc(S(C)(=O)=O)c2c1[C@@H](F)C(F)(F)[C@H]2O)C(F)(F)F]

The following examples relate to medicaments:

Example A: Injection Vials

A solution of 100 g of an active ingredient of the formula I and 5 g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active ingredient.

Example B: Suppositories

A mixture of 20 g of an active ingredient of the formula I with 100 g of soya lecithin and 1400 g of cocoa butter is melted, poured into moulds and allowed to cool. Each suppository contains 20 mg of active ingredient.

Example C: Solution

A solution is prepared from 1 g of an active ingredient of the formula I, 9.38 g of $NaH_2PO_4 \cdot 2H_2O$, 28.48 g of $Na_2HPO_4 \cdot 12\ H_2O$ and 0.1 g of benzalkonium chloride in 940 mL of bidistilled water. The pH is adjusted to 6.8, and the solution is made up to 1 l and sterilised by irradiation. This solution can be used in the form of eye drops.

Example D: Ointment 500 mg of an active ingredient of the formula I are mixed with 99.5 g of Vaseline under aseptic conditions.

Example E: Tablets

A mixture of 1 kg of active ingredient of the formula I, 4 kg of lactose, 1.2 kg of potato starch, 0.2 kg of talc and 0.1 kg of magnesium stearate is pressed in a conventional manner to give tablets in such a way that each tablet contains 10 mg of active ingredient.

Example F: Dragees

Tablets are pressed analogously to Example E and subsequently coated in a conventional manner with a coating of sucrose, potato starch, talc, tragacanth and dye.

Example G: Capsules 2 kg of active ingredient of the formula I are introduced into hard gelatine capsules in a conventional manner in such a way that each capsule contains 20 mg of the active ingredient.

Example H: Ampoules

A solution of 1 kg of active ingredient of the formula I in 60 l of bidistilled water is sterile filtered, transferred into ampoules, lyophilised under sterile conditions and sealed under sterile conditions. Each ampoule contains 10 mg of active ingredient.

The invention claimed is:

1. A compound of the formula I

I

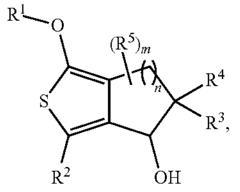

wherein $R^1$ denotes A or $[C(R^6)_2]_q$Cyc, $R^2$ denotes $SO_2A$, $R^3$ denotes H or Hal, $R^4$ denotes H or Hal, $R^5$ denotes H or Hal, $R^6$ denotes H or A', A denotes unbranched or branched alkyl having 1-8 C-atoms, in which 1-5 H atoms may be replaced by OH, O—$C_{1-8}$-alkyl which alkyl may be unbranched or branched, F, Cl, and/or Br, and/or in which one or two non-adjacent $CH_2$ groups may be replaced by O and/or NH groups, A' denotes unbranched or branched alkyl having 1, 2, 3, or 4 C-atoms, Cyc denotes cyclic alkyl with 3, 4, 5, 6, or 7 C-atoms, in which 1-5 H atoms may be replaced by OH, OA, F, and/or Cl, Hal denotes F, Cl, Br, or I, n denotes 1 or 2, m denotes 0, 1, 2, or 3, q denotes 0, 1, or 2, or a pharmaceutically acceptable solvate, salt, tautomer, or stereoisomer thereof, including a mixture thereof in all ratios.

2. The compound according to claim 1, wherein $R^1$ is $[C(R^6)_2]_q$Cyc, or a pharmaceutically acceptable solvate, salt, tautomer, or stereoisomer thereof, including a mixture thereof in all ratios.

3. The compound according to claim 1, wherein $R^2$ denotes $SO_2A$, wherein A is unbranched or branched alkyl having 1-8 C— atoms, or a pharmaceutically acceptable solvate, salt, tautomer, or stereoisomer thereof, including a mixture thereof in all ratios.

4. The compound according to claim 1, wherein $R^3$ denotes H or F, $R^4$ denotes H or F, $R^5$ denotes H, or a pharmaceutically acceptable solvate, salt, tautomer, or stereoisomer thereof, including a mixture thereof in all ratios.

5. The compound according to claim 1, wherein

A denotes unbranched or branched alkyl having 1-8 C-atoms, in which 1-5 H atoms may be replaced by OH and/or F, and/or in which one or two non-adjacent $CH_2$ groups may be replaced by O and/or NH groups, or a pharmaceutically acceptable solvate, salt, tautomer, or stereoisomer thereof, including a mixture thereof in all ratios.

6. The compound according to claim 1, wherein

Ar denotes phenyl, which is unsubstituted or mono-, di-, or trisubstituted by Hal and/or CN, or a pharmaceutically acceptable solvate, salt, tautomer, or stereoisomer thereof, including a mixture thereof in all ratios.

7. The compound according to claim 1, wherein

Het denotes a monocyclic saturated heterocycle having 1 to 4 N, O, and/or S atoms, which may be unsubstituted or mono-, di-, or trisubstituted by Hal, A, CN, OH, and/or OA, or a pharmaceutically acceptable solvate, salt, tautomer, or stereoisomer thereof, including a mixtures thereof in all ratios.

8. The compound according to claim 1, wherein

Het denotes tetrahydrofuryl, 1,3-dioxolanyl, tetrahydrothienyl, pyrrolidinyl, piperidinyl, morpholinyl, tetrahydro-pyranyl, or piperazinyl, or a pharmaceutically acceptable solvate, salt, tautomer, or stereoisomer thereof, including a mixture thereof in all ratios.

9. The compound according to claim 1, wherein $R^1$ denotes A or $[C(R^6)_2]_q$Cyc, $R^2$ denotes $SO_2A$, $R^3$ denotes H or F, $R^4$ denotes H or F, $R^5$ denotes H, $R^6$ denotes H or A', A denotes unbranched or branched alkyl having 1-8 C-atoms, in which 1-5 H atoms may be replaced by OH and/or F, and/or in which one or two non-adjacent $CH_2$ groups may be replaced by O and/or NH groups, A' denotes unbranched or branched alkyl having 1, 2, 3, or 4 C-atoms, Cyc denotes cyclic alkyl with 3, 4, 5, 6, or 7 C-atoms, in which 1-5 H atoms may be replaced by OH, OA, F, and/or Cl, Hal denotes F, Cl, Br, or I, n denotes 1 or 2, m denotes 0, 1, 2, or 3, q denotes 0, 1, or 2, or a pharmaceutically acceptable solvate, salt, tautomer, or stereoisomer thereof, including a mixture thereof in all ratios.

10. A compound selected from the group consisting of:

| No. | Structure |
|---|---|
| 1a | (4S)-1-(cyclohexyloxy)-5,5-difluoro-3-methanesulfonyl-4H,5H,6H-cyclopenta[c]thiophen-4-ol, |
| 2a | (4S)-1-(2,2-dimethylpropoxy)-5,5-difluoro-3-methanesulfonyl-4H,5H,6H-cyclopenta[c]thiophen-4-ol, |
| 3a | (4S)-1-cyclobutoxy-5,5-difluoro-3-methanesulfonyl-4H,5H,6H-cyclopenta[c]thiophen-4-ol, |
| 4a | (4S)-5,5-difluoro-3-methanesulfonyl-1-(2-methylbutoxy)-4H,5H,6H-cyclopenta[c]thiophen-4-ol, |
| 5a | (4S)-1-(2,2-difluoroethoxy)-5,5-difluoro-3-methanesulfonyl-4H,5H,6H-cyclopenta[c]thiophen-4-ol, |
| 6a | (4S)-5,5-difluoro-3-methanesulfonyl-1-(3,3,3-trifluoro-2-methylpropoxy)-4H,5H,6H-cyclopenta[c]thiophen-4-ol, |
| 7a | (4S)-5,5-difluoro-3-methanesulfonyl-1-(2,2,2-trifluoroethoxy)-4H,5H,6H-cyclopenta[c]thiophen-4-ol, |
| 8a | (4S)-5,5-difluoro-3-methanesulfonyl-1-(2-methylpropoxy)-4H,5H,6H-cyclopenta[e]thiophen-4-ol, |
| 9a | (4S)-5,5-difluoro-3-methanesulfonyl-1-{[1,1,1-trifluorobutan-2-yl]oxy}-4H,5H,6H-cyclopenta[c]thiophen-4-ol, |
| 10a | (4S)-1-{[1,1-difluoropropan-2-yl]oxy}-5,5-difluoro-3-methanesulfonyl-4H,5H,6H-cyclopenta[c]thiophen-4-ol, |
| 11a | (4S)-5,5-difluoro-3-methanesulfonyl-1-(3,3,3-trifluoropropoxy)-4H,5H,6H-cyclopenta[c]thiophen-4-ol, |
| 12a | (4S)-5,5-difluoro-3-methanesulfonyl-1-propoxy-4H,5H,6H-cyclopenta[c]thiophen-4-ol, |
| 13a | (4S)-1-(cyclopropylmethoxy)-5,5-difluoro-3-methanesulfonyl-4H,5H,6H-cyclopenta[c]thiophen-4-ol, |
| 14a | (4S)-1-{[1,1-difluoropropan-2-yl]oxy}-5,5-difluoro-3-methanesulfonyl-4H,5H,6H-cyclopenta[c]thiophen-4-ol, |
| 15a | (4S)-1-(2,2-difluoropropoxy)-5,5-difluoro-3-methanesulfonyl-4H,5H,6H-cyclopenta[c]thiophen-4-ol, |
| 16a | (4S)-5,5-difluoro-3-methanesulfonyl-1-[(1-methoxycyclobuty])methoxy]-4H,5H,6H-cyclopenta[c]thiophen-4-ol, |
| 17a | (4S,5S)-5-fluoro-3-methanesulfonyl-1-(2,2,2-trifluoroethoxy)-4H,5H,6H-cyclopenta[c]thiophen-4-ol, |
| 18a | (4S)-1-[(3,3-difluorocyclobuty])methoxy]-5,5-difluoro-3-methanesulfonyl-4H,5H,6H-cyclopenta[c]thiophen-4-ol, |
| 19a | (4S)-1-(cyclobutylmethoxy)-5,5-difluoro-3-methanesulfonyl-4H,5H,6H-cyclopenta[c]thiophen-4-ol, |
| 20a | (4S)-1-(1-cyclobutylethoxy)-5,5-difluoro-3-methanesulfonyl-4H,5H,6H-cyclopenta[c]thiophen-4-ol, |
| 21a | (4S)-1-(3,3-difluorobutoxy)-5,5-difluoro-3-methanesulfonyl-4H,5H,6H-cyclopenta[c]thiophen-4-ol, |
| 22a | (4S)-5,5-difluoro-3-methanesulfonyl-1-(oxan-4-yloxy)-4H,5H,6H-cyclopenta[c]thiophen-4-ol, |
| 23a | (4S)-5,5-difluoro-3-methanesulfonyl-1-[2-(trifluoromethoxy)ethoxy]-4H,5H,6H-cyclopenta[c]thiophen-4-ol, |
| 24a | 1-(3,4-difluorophenoxy)-5,5-difluoro-3-methanesulfonyl-4H,5H,6H-cyclopenta[c]thiophen-4-ol, |
| 25a | (4S)-5,5-difluoro-3-methanesulfonyl-1-(propan-2-yloxy)-4H,5H,6H-cyclopenta[c]thiophen-4-ol, |
| 26a | 3-chloro-5-{(4S)-5,5-difluoro-4-hydroxy-3-methanesulfonyl-4H,5H,6H-cyclopenta[c]thiophen-1-yl]oxy}benzonitrile, |
| 27a | (4S)-1-(3,5-difluorophenoxy)-5,5-difluoro-3-methanesulfonyl-4H,5H,6H-cyclopenta[c]thiophen-4-ol, |
| 26a | 3-{[(4S)-5,5-difluoro-4-hydroxy-3-methanesulfonyl-4H,5H,6H-cyclopenta[c]thiophen-1-yl]oxy}-5-fluorobenzonitrile, |
| 29a | (4S)-5,5-difluoro-1-(4-fluorophenoxy)-3-methanesulfonyl-4H,5H,6H-cyclopenta[c]thiophen-4-ol, |
| 30a | (4S)-1-(3-chloro-5-fluorophenoxy)-5,5-difluoro-3-methanesulfonyl-4H,5H,6H-cyclopenta[c]thiophen-4-ol, |
| 31a | 3-{[(4S)-5,5-difluoro-4-hydroxy-3-methanesulfonyl-4H,5H,6H-cyclopenta[c]thiophen-1-yl]oxy}benzonitrile, |
| 32a | (4S)-1-ethoxy-5,5-difluoro-3-methanesulfonyl-4H,5H,6H-cyclopenta[c]thiophen-4-ol, |
| 33a | (4S)-5,5-difluoro-3-methanesulfonyl-1-(4,4,4-trifluorobutoxy)-4H,5H,6H-cyclopenta[c]thiophen-4-ol, and |
| 34a | (4S)-1-(3,4-difluorophenoxy)-5,5-difluoro-3-methanesulfonyl-4H,5H,6H-cyclopenta[c]thiophen-4-ol; |

or a pharmaceutically acceptable solvate, salt, tautomer or stereoisomer thereof, including a mixture thereof in all ratios.

11. A process for the preparation of the compound of the formula I according to claim 1 or a pharmaceutically acceptable salt, solvate, tautomer, or stereoisomer thereof, the process comprising:

reacting a compound of the formula II with $NaBH_4$ or any other reducing agent,

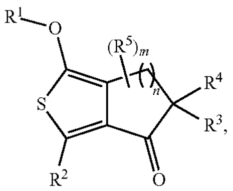

II wherein $R^1$, $R^2$, $R^3$, $R^4$, $R^5$, n, and m have the meanings indicated in claim 1, and/or converting a base or acid of the formula I into one of its salts.

12. A medicament, comprising:

at least one compound of the formula I according to claim 1 and/or a pharmaceutically acceptable salt, solvate, tautomer, or stereoisomer thereof, including a mixture thereof in all ratios, and optionally, a pharmaceutically acceptable carrier, excipient, or vehicle.

13. A method for the treatment and/or prevention of cancer and/or von Hippel-Lindau disease (VHL), the method comprising:

administering to a subject in need thereof, the compound of the formula I according to claim 1 and/or a pharmaceutically acceptable salt, solvate, tautomer, or stereoisomer thereof, including a mixture thereof in all ratios.

14. The method wherein the cancer is a cancer of head, neck, eye, mouth, throat, esophagus, bronchus, larynx, pharynx, chest, bone, lung, colon, rectum, stomach, prostate, urinary bladder, uterine, cervix, breast, ovaries, testicles or other reproductive organs, skin, thyroid, blood, lymph nodes, kidney, liver, pancreas, brain, or central nervous system, or wherein the cancer is a solid tumor, blood-borne tumor, glioblastoma, renal cell carcinoma (RCC), or clear cell renal cell carcinoma (ccRCC).

15. A medicament, comprising:

at least one compound of the formula I according to claim 1 and/or a pharmaceutically acceptable salt, solvate, or stereoisomer thereof, including a mixture thereof in all ratios, and at least one further medicament active ingredient.

16. A set (kit) consisting of separate packs of (a) an effective amount of the compound of the formula I according to claim 1 and/or a pharmaceutically acceptable salt, solvate, tautomer, or stereoisomer thereof, including a mixture thereof in all ratios, and (b) an effective amount of a further medicament active ingredient.

* * * * *